United States Patent
Xu et al.

(10) Patent No.: US 6,764,843 B2
(45) Date of Patent: Jul. 20, 2004

(54) **METHOD OF CLONING AND EXPRESSION OF BSMBI RESTRICTION ENDONUCLEASE AND BSMBI METHYLASE IN *E. COLI* AND PURIFICATION OF BSMBI ENDONUCLEASE**

(75) Inventors: Shuang-yong Xu, Lexington, MA (US); Andrew Dore, Salem, MA (US); Adam Hume, Lewiston, MN (US); John Pelletier, Amesbury, MA (US); Jing Zhou, Beverly, MA (US)

(73) Assignee: New England Biolabs, Inc., Beverly, MA (US)

( * ) Notice: Subject to any disclaimer, the term of this patent is extended or adjusted under 35 U.S.C. 154(b) by 105 days.

(21) Appl. No.: 09/966,997

(22) Filed: Sep. 28, 2001

(65) Prior Publication Data

US 2003/0100052 A1 May 29, 2003

(51) Int. Cl.⁷ .............................. C12N 9/22; C12N 15/55
(52) U.S. Cl. ................. 435/199; 435/320.1; 435/252.3; 536/23.2
(58) Field of Search .............................. 435/199, 320.1, 435/252.3; 536/23.3

(56) References Cited

U.S. PATENT DOCUMENTS 5,200,333 A  4/1993  Wilson .................... 435/172.3
5,498,535 A  3/1996  Fomenkov et al. ....... 435/172.3

OTHER PUBLICATIONS

Roberts and Macelis, Nucl. Acids Res. 27: 312–313, (1999).
Kosykh et al., Mol. Gen. Genet. 178: 717–719, (1980).
Mann et al., Gene 3: 97–112, (1978).
Walder et al., Proc. Natl. Acad. Sci. 78: 1503–1507, (1981).
Bougueleret et al., Nucl. Acids Res. 12: 3659–3676, (1984).
Gingeras and Brooks, Proc. Natl. Acad. Sci. USA 80: 402–406, (1983).
Theriault and Roy, Gene 19: 355–359 (1982).
Blumenthal et al., J. Bacteriol. 164: 501–509, (1985).
Wayne et al. Gene 202: 83–88, (1997).
Kiss et al., Nucl. Acids Res. 13: 6403–6421, (1985).
Szomolanyi et al., Gene 10: 219–225, (1980).
Janulaitis et al., Gene 20: 197–204 (1982).
Kiss and Baldauf, Gene 21: 111–119, (1983).
Fomenkov et al., Nucl. Acids Res. 22: 2399–2403, (1994).
Malone et al., J. Mol. Biol. 253: 618–632, (1995).
New England Biolabs' Catalog, Jan. 2001, p. 220.

*Primary Examiner*—Charles L. Patterson, Jr.
(74) *Attorney, Agent, or Firm*—Gregory D. Williams

(57) ABSTRACT

The present invention relates to recombinant DNA that encodes the BsmBI restriction endonuclease as well as BsmBI methyltransferase, expression of BsmBI restriction endonuclease and BsmBI methylase in *E. coli* cells containing the recombinant DNA. It also relates to a method for purification of the recombinant BsmBI restriction endonuclease.

6 Claims, 8 Drawing Sheets

FIG. 2A

```
     ATGAACTCCTTATCACTAAAAGATGAAATGGAGATTTGGAAACAAGCTTCTAATATTCGA
  1  ------------+---------+---------+---------+---------+---------+  60
      M  N  S  L  S  L  K  D  E  M  E  I  W  K  Q  A  S  N  I  R
     AAAAAAATTGCAATGGAAACGGCGGCGGAATTTTTAAATGAATTTAATGCTGAAAAAGCA
 61  ------------+---------+---------+---------+---------+---------+ 120
      K  K  I  A  M  E  T  A  A  E  F  L  N  E  F  N  A  E  K  A
     CTTAAGCAAATAAAAAATTCAATTCTAAATCCGCTCTATGAAAGGAATCCTTTTCAAAAT
121  ------------+---------+---------+---------+---------+---------+ 180
      L  K  Q  I  K  N  S  I  L  N  P  L  Y  E  R  N  P  F  Q  N
     ACATTGGAAAAGCTTTCTTTCTCTCTATATTTAACAGAAAAAATCTATAGATTATGTTCTT
181  ------------+---------+---------+---------+---------+---------+ 240
      T  L  E  K  L  S  F  S  L  Y  L  T  E  K  S  I  D  Y  V  L
     CAAATGGAAGTGGAGCCTATAAAGAAATTATCATATGCCAATTTTTTTGTTGAGATAGGA
241  ------------+---------+---------+---------+---------+---------+ 300
      Q  M  E  V  E  P  I  K  K  L  S  Y  A  N  F  F  V  E  I  G
     GCAAGGGAGTTTATCTCACCTTTTCATCCTGATAAAATTGAGAAGAATTTAACAGCTTCA
301  ------------+---------+---------+---------+---------+---------+ 360
      A  R  E  F  I  S  P  F  H  P  D  K  I  E  K  N  L  T  A  S
     AAAGCTTATGGATATTTTTTCACACCAATTTCATTAGGGACAAGAATGGTTAAGTTAGCT
361  ------------+---------+---------+---------+---------+---------+ 420
      K  A  Y  G  Y  F  F  T  P  I  S  L  G  T  R  M  V  K  L  A
     TTAAAAGATAAACCTAAAAATCTAAAATCTATAGTTGACCCTGCCTGTGGTATAGGCAGT
421  ------------+---------+---------+---------+---------+---------+ 480
      L  K  D  K  P  K  N  L  K  S  I  V  D  P  A  C  G  I  G  S
     TTACTAGCATTGGCTCTAATATATAATCCAGAAATAGAAAATGTTGTAGGAATAGAATTG
481  ------------+---------+---------+---------+---------+---------+ 540
      L  L  A  L  A  L  I  Y  N  P  E  I  E  N  V  V  G  I  E  L
     GATAGCTTTACCGCTAATATTTCCCATAAATTACTTGTTAGAATAAGTAAAGACTTAGGA
541  ------------+---------+---------+---------+---------+---------+ 600
      D  S  F  T  A  N  I  S  H  K  L  L  V  R  I  S  K  D  L  G
     ATAACACCTAAGATTAAGATAATTAATCAAAATTTCTTGGACTACGTTTTGAACTATGAA
601  ------------+---------+---------+---------+---------+---------+ 660
      I  T  P  K  I  K  I  I  N  Q  N  F  L  D  Y  V  L  N  Y  E
     GAAGAACATAAGGAAAAGTTTGATTTGCTTATTATGAATCCCCCTTATGGAAGGGTGAGA
661  ------------+---------+---------+---------+---------+---------+ 720
      E  E  H  K  E  K  F  D  L  L  I  M  N  P  P  Y  G  R  V  R
     TTCCTGAAAAATTCTTTAACTAATAAAGAAACTAAAAGTGGGCTTACTGAGGGAATCTCT
721  ------------+---------+---------+---------+---------+---------+ 780
      F  L  K  N  S  L  T  N  K  E  T  K  S  G  L  T  E  G  I  S
     GAGTTAGAAAAAAAGCTTAGAGAAGAAACAATCCTTAACGCAGCGGATTTACGGAAGAAA
781  ------------+---------+---------+---------+---------+---------+ 840
      E  L  E  K  K  L  R  E  E  T  I  L  N  A  A  D  L  R  K  K
     TTTGCATCGGTTGGACTTGGAAAGGGGACCCCTGAATATTCAAAGGTATTCCTAGCTATT
841  ------------+---------+---------+---------+---------+---------+ 900
      F  A  S  V  G  L  G  K  G  T  P  E  Y  S  K  V  F  L  A  I
     TCAACAAAGATAGTAAAGCAAAATGGTTATGTTATTGCAATAACCCCATCATCATGGTTA
901  ------------+---------+---------+---------+---------+---------+ 960
      S  T  K  I  V  K  Q  N  G  Y  V  I  A  I  T  P  S  S  W  L
```

FIG. 2B

```
           GGTGATGAAAGTGGAAGAGAACTAAGAAAGTATTTAGTTGAGAATCATGGAATCTCATGT
  961      ------+---------+---------+---------+---------+---------+  1020
            G D E S G R E L R K Y L V E N H G I S C
           ATATGGAATTTTAAAGAAAGTGCTAAATTATTTTCAGGTGTTAATCAACCTACAACCGTT
 1021      ------+---------+---------+---------+---------+---------+  1080
            I W N F K E S A K L F S G V N Q P T T V
           GTAAAAATTAAAGTTAATTCAAATGAATCAAAGATAGAAATTCAAGGTCCTCTATCTTCT
 1081      ------+---------+---------+---------+---------+---------+  1140
            V K I K V N S N E S K I E I Q G P L S S
           CTAGAAGAACTAGGAAGGGATATCCAGTATTTGGACACATGTAATATAAAAAAATACAGT
 1141      ------+---------+---------+---------+---------+---------+  1200
            L E E L G R D I Q Y L D T C N I K K Y S
           CCAGAATGGTATAGAATACCCCAATGCGGGAATGAGCGAGCAAAAATACTTTCTAAATTG
 1201      ------+---------+---------+---------+---------+---------+  1260
            P E W Y R I P Q C G N E R A K I L S K L
           CATAATCATGCCCCCTTATCTTCACACAAAAAAATCTATAATCTTAGAGGAGAGTTAGAT
 1261      ------+---------+---------+---------+---------+---------+  1320
            H N H A P L S S H K K I Y N L R G E L D
           TTAACATCTCATAAAGATTTATTAAGTGATAATCCGAATCATTGGAGACTTATTAGGGGA
 1321      ------+---------+---------+---------+---------+---------+  1380
            L T S H K D L L S D N P N H W R L I R G
           GACCATGTTGAAAAATTTAATTTAAAGAATCCAGAGGAATCAGAAAAGCTAGGATTTGTT
 1381      ------+---------+---------+---------+---------+---------+  1440
            D H V E K F N L K N P E E S E K L G F V
           GACCATCAATTATTTATTAAAAGAATGGGAAAAAGTAATAAGTTAAGACACATTAAAAAC
 1441      ------+---------+---------+---------+---------+---------+  1500
            D H Q L F I K R M G K S N K L R H I K N
           TGGAGAATAACACTTCCACAATGTTCTTATATGAATAAAAAGAAGCGGATAGAGGCATGC
 1501      ------+---------+---------+---------+---------+---------+  1560
            W R I T L P Q C S Y M N K K K R I E A C
           ATAGTAGAACCAAATAATATAATTGCAAATTCATGTAATTATATCACTTTAGAAGATTGT
 1561      ------+---------+---------+---------+---------+---------+  1620
            I V E P N N I I A N S C N Y I T L E D C
           AACGAATTGGTAGACAACTTACTGTTACTCTGTGCAATTATAAATAGTGCTGTAATAGAG
 1621      ------+---------+---------+---------+---------+---------+  1680
            N E L V D N L L L L C A I I N S A V I E
           TGGAGATTTAGATTGTTCAATAGTAATAATCATGTGTCAAATTATGAGATTGATGAATTT
 1681      ------+---------+---------+---------+---------+---------+  1740
            W R F R L F N S N N H V S N Y E I D E F
           CCAATATTTAAATTTGATACTGAAACTGAAATGTTGACTATGTTAAAAGGTTTTTTGCAT
 1741      ------+---------+---------+---------+---------+---------+  1800
            P I F K F D T E T E M L T M L K G F L H
           AAGCCCATAGAAAATTGGTCTAAAATAGAAGCTCTTATAGCTTTAATGTATGGATTGAAT
 1801      ------+---------+---------+---------+---------+---------+  1860
            K P I E N W S K I E A L I A L M Y G L N
           ATAGAAGATATGAAAGTAATACTGAATGATTTAGAATATGAAGATAAAGATAAAATATTA
 1861      ------+---------+---------+---------+---------+---------+  1920
            I E D M K V I L N D L E Y E D K D K I L
```

FIG. 2C

```
     AAATATATGGATATTTATCAAGAGAAATTTAGTAATAAAGACTTTATAGTTTATAACCAT
1921 ------------------------------------------------------------ 1980
      K  Y  M  D  I  Y  Q  E  K  F  S  N  K  D  F  I  V  Y  N  H
     ACTTTACCAACACTTTCAGAATTAGATAAAGAGATGATTTCATATGTTAAACAAGGGGGG
1981 ------------------------------------------------------------ 2040
      T  L  P  T  L  S  E  L  D  K  E  M  I  S  Y  V  K  Q  G  G
     AACTGGGAGGACATTCCTGAAACTGTTCCTTCAAAGAGATTAGAACAGATAAGAGAAATG
2041 ------------------------------------------------------------ 2100
      N  W  E  D  I  P  E  T  V  P  S  K  R  L  E  Q  I  R  E  M
     AGTAAGAGAAGAGGAAAAGTTAGGACTACCTATTATGGTAGATTAAACCCTAATCAACCT
2101 ------------------------------------------------------------ 2160
      S  K  R  R  G  K  V  R  T  T  Y  Y  G  R  L  N  P  N  Q  P
     GCTTATACAATATCCACTTATTTTAATAGGCCGGGAAATGGAACGAATATTCATCCTTGG
2161 ------------------------------------------------------------ 2220
      A  Y  T  I  S  T  Y  F  N  R  P  G  N  G  T  N  I  H  P  W
     GAAAATAGGACCATAAGTTGCAGAGAAGCTGCGAGATTACAATCATTTCCTGATAGTTTT
2221 ------------------------------------------------------------ 2280
      E  N  R  T  I  S  C  R  E  A  A  R  L  Q  S  F  P  D  S  F
     ATCTTCTATGGGAAGGAGGGAGCAGTTAGAAAACAGATAGGTAATGCCGTTCCTCCATTA
2281 ------------------------------------------------------------ 2340
      I  F  Y  G  K  E  G  A  V  R  K  Q  I  G  N  A  V  P  P  L
     TTAAGTTATGCTTTAGGTAAGACAATAAAAGCTAAAACATTTGTAGATTTATTTGCTGGA
2341 ------------------------------------------------------------ 2400
      L  S  Y  A  L  G  K  T  I  K  A  K  T  F  V  D  L  F  A  G
     GCAGGCGGACTTAGCTATGGTTTTGAACTTGCTGGATTAGAAGGGATGGCAGCCTTAGAG
2401 ------------------------------------------------------------ 2460
      A  G  G  L  S  Y  G  F  E  L  A  G  L  E  G  M  A  A  L  E
     ATTGATAAAGATGCCGCTGAAACTTATGCAAAAAATCATTCATCTAATATAGACGTAATA
2461 ------------------------------------------------------------ 2520
      I  D  K  D  A  A  E  T  Y  A  K  N  H  S  S  N  I  D  V  I
     GTCGGTGATATCAGAAGCCCAGAAATACAAAATCAATTAATTGAGTCAGTGAAAAACAAG
2521 ------------------------------------------------------------ 2580
      V  G  D  I  R  S  P  E  I  Q  N  Q  L  I  E  S  V  K  N  K
     TTAAAGGGTCGAACTTTAGATTTAATTGCTGGTGGTCTTCCTTGTCAAGGCTTTTCAACA
2581 ------------------------------------------------------------ 2640
      L  K  G  R  T  L  D  L  I  A  G  G  L  P  C  Q  G  F  S  T
     GCAGGATGGAGAAAGCCAGATGATGAGAGGAATGCTTTAGTCACTTATTTTTTGCAGGTT
2641 ------------------------------------------------------------ 2700
      A  G  W  R  K  P  D  D  E  R  N  A  L  V  T  Y  F  L  Q  V
     GTTCAGAAGTTAATGCCAAATTACGTTTTAATAGAAAACGTAGAAGGGCTTATTAATATG
2701 ------------------------------------------------------------ 2760
      V  Q  K  L  M  P  N  Y  V  L  I  E  N  V  E  G  L  I  N  M
     AATAAAGGATTAGTACTTAAAAGTATTCATGAAGTATTAGATGAGTTGGGCTATATTTAC
2761 ------------------------------------------------------------ 2820
      N  K  G  L  V  L  K  S  I  H  E  V  L  D  E  L  G  Y  I  Y
     TATAAGAATCCTTGGGTATTAAGTGCGGAACAATATGGGGTACCTCAAATGAGAAAAAGG
2821 ------------------------------------------------------------ 2880
      Y  K  N  P  W  V  L  S  A  E  Q  Y  G  V  P  Q  M  R  K  R
```

FIG. 2D

```
     GTTTTTATTGTAGCCGCAAAAAAAGGATTAGAATTACCAAAACCACCAGTTCAATACTTT
2881 ------------+---------+---------+---------+---------+---------+ 2940
      V F I V A A K K G L E L P K P P V Q Y F
     GACAAGTGTCTCGGTAGACGTGAAAAAGAATCGGATAGGAAAACTGATAGATATCCAGTA
2941 ------------+---------+---------+---------+---------+---------+ 3000
      D K C L G R R E K E S D R K T D R Y P V
     ACAGTTGCGGAAGCCTTCTTTGGACTACCTTGCTTATTAAGTCCGGTATTTACTCCTCCG
3001 ------------+---------+---------+---------+---------+---------+ 3060
      T V A E A F F G L P C L L S P V F T P P
     TTAGAGATTAACCCTTTGTACAGTCAATGGTGTAATAATATTATCACTACTGAAGAGTTT
3061 ------------+---------+---------+---------+---------+---------+ 3120
      L E I N P L Y S Q W C N N I I T T E E F
     CTTAATAAGAGAGGTAAAATTAAAATTGAGCAAGAAGAACTAGATGCTCCACAACTAAAA
3121 ------------+---------+---------+---------+---------+---------+ 3180
      L N K R G K I K I E Q E E L D A P Q L K
     GTAGAACAACTAGAATTTACCTTTTAA
3181 ------------+---------+------- 3207
      V E Q L E F T F *
```

FIG. 3A

```
    TTGGCTAAATACGGACGTGGAAAGTTTTTACCTCATCAAAACTATATCGATTATATGCAT
 1  ------+---------+---------+---------+---------+---------+  60
     M  A  K  Y  G  R  G  K  F  L  P  H  Q  N  Y  I  D  Y  M  H
    TTTATAGTGAACCATAAGAATTATTCTGGTATGCCAAACGCTATTGGAGAGGATGGAAGA
61  ------+---------+---------+---------+---------+---------+  120
     F  I  V  N  H  K  N  Y  S  G  M  P  N  A  I  G  E  D  G  R
    ATAAATTGGCAGGTAAGCTCTGGAAAAACAACGTCTTTTTATGAATATTATCAAGCAAGA
121 ------+---------+---------+---------+---------+---------+  180
     I  N  W  Q  V  S  S  G  K  T  T  S  F  Y  E  Y  Y  Q  A  R
    TTTGAATGGTGGGAGAAGAAAGCTGATGAACTTAATTTACCTGGAACGGGTAATTCAAAC
181 ------+---------+---------+---------+---------+---------+  240
     F  E  W  W  E  K  K  A  D  E  L  N  L  P  G  T  G  N  S  N
    AAAAGGTTTTCTTTAGCAGCAAGGTTAATTCATCCTACAGGACAAAGGCCGTGTAGATTA
241 ------+---------+---------+---------+---------+---------+  300
     K  R  F  S  L  A  A  R  L  I  H  P  T  G  Q  R  P  C  R  L
    TGTGGTAAGTACCAATATGTTGGTTACATGTATGTTTCACACAACCTTTACAAACGATGG
301 ------+---------+---------+---------+---------+---------+  360
     C  G  K  Y  Q  Y  V  G  Y  M  Y  V  S  H  N  L  Y  K  R  W
    AGTAAGATAACAGGTAGAGAAGACCTTTTTTTTAAAAAAACAGAATATCATTGAGGCAGCT
361 ------+---------+---------+---------+---------+---------+  420
     S  K  I  T  G  R  E  D  L  F  F  K  K  Q  N  I  I  E  A  A
    AACATTTTTAAATCTATTATGGGAGAACAAGCACTTATTAATGAATTAACAACCATTTTT
421 ------+---------+---------+---------+---------+---------+  480
     N  I  F  K  S  I  M  G  E  Q  A  L  I  N  E  L  T  T  I  F
    CCAGAAAGAAAAGATTATTTCAACAGATTACCAAACATTGAAGATTTCTTTGTAAGTTCT
481 ------+---------+---------+---------+---------+---------+  540
     P  E  R  K  D  Y  F  N  R  L  P  N  I  E  D  F  F  V  S  S
    AGTCACATAAAAAATAATGGAAATTATATTAGTCCAGGATTTATGGCTAATCCGCCTGAC
541 ------+---------+---------+---------+---------+---------+  600
     S  H  I  K  N  N  G  N  Y  I  S  P  G  F  M  A  N  P  P  D
    CGACTAGACGGATTTCACGATTATGGAATCTGTTGTAGGAAAGAAAAAGACCCAGGGCGA
601 ------+---------+---------+---------+---------+---------+  660
     R  L  D  G  F  H  D  Y  G  I  C  C  R  K  E  K  D  P  G  R
    CATGACGATAACATGAGACTATATAATCATGATAGACGTGCTTTTATGTGGTGGTCAGAA
661 ------+---------+---------+---------+---------+---------+  720
     H  D  D  N  M  R  L  Y  N  H  D  R  R  A  F  M  W  W  S  E
    GGTGATTGGGCACTTGCAGACGCACTATATAATAAAGCTGGGGCTGGAAAATGTGCTGAC
721 ------+---------+---------+---------+---------+---------+  780
     G  D  W  A  L  A  D  A  L  Y  N  K  A  G  A  G  K  C  A  D
    CCAGATTGTCAAAAAGAAGTTGAAAAAAATAAGCCCTGACCATGTTGGCCCTATCTCTTGT
781 ------+---------+---------+---------+---------+---------+  840
     P  D  C  Q  K  E  V  E  K  I  S  P  D  H  V  G  P  I  S  C
    GGTTTTAAACAGATTCCTTTTTTTTAAACCACTCTGTGCATCATGTAACTCAGCAAAAAAT
841 ------+---------+---------+---------+---------+---------+  900
     G  F  K  Q  I  P  F  F  K  P  L  C  A  S  C  N  S  A  K  N
    CGTAGGTTTTCATATCAAGATGTAAAGGAATTATTAAAATATGAAAACTACACAGGAGAT
901 ------+---------+---------+---------+---------+---------+  960
     R  R  F  S  Y  Q  D  V  K  E  L  L  K  Y  E  N  Y  T  G  D
```

FIG. 3B

```
     TCGGTTGCTTCATGGCAAGTGCGGGCTTTATGGGATAACTGTAAACATTTAGTAAAAAAT
961  ------------+----------+----------+----------+----------+ 1020
     S  V  A  S  W  Q  V  R  A  L  W  D  N  C  K  H  L  V  K  N
     GACGATGATTCCAAATTACTTAGCAATTTAATGAGAAGCTTGCAAGACTACTATTTACGG
1021 ------------+----------+----------+----------+----------+ 1080
     D  D  D  S  K  L  L  S  N  L  M  R  S  L  Q  D  Y  Y  L  R
     TCTCTATATAAATTGTTTTCGAATGGCTTTGCACATCTTCTATCTTACTTCCTCACACCC
1081 ------------+----------+----------+----------+----------+ 1140
     S  L  Y  K  L  F  S  N  G  F  A  H  L  L  S  Y  F  L  T  P
     GAATATGCACATTATAAAATTACTTTTGAGGGATTAAATACAAGCACTCTAGAATATGAA
1141 ------------+----------+----------+----------+----------+ 1200
     E  Y  A  H  Y  K  I  T  F  E  G  L  N  T  S  L  E  Y  E
     CGATACTACAAAACTTTTAAAAAGACTAAATCGACGTCTAGTTTGGCTGCACGAATTGTT
1201 ------------+----------+----------+----------+----------+ 1260
     R  Y  Y  K  T  F  K  K  T  K  S  T  S  S  L  A  A  R  I  V
     AGAATTGCATTTGAGGAACTAGAAATATATAATTCTAAGGATATAAATGAGAGAAAGTTA
1261 ------------+----------+----------+----------+----------+ 1320
     R  I  A  F  E  E  L  E  I  Y  N  S  K  D  I  N  E  R  K  L
     ATTAAATTTGACACTTCAAGTTGGGAAAAGGACTTTGAGAATATAATATCCTATGCTACC
1321 ------------+----------+----------+----------+----------+ 1380
     I  K  F  D  T  S  S  W  E  K  D  F  E  N  I  I  S  Y  A  T
     AAAAACTTATCTTTGGATGAAGAAGCATCAAAATGGAATAAGGTTTTAACTGATAAGAAT
1381 ------------+----------+----------+----------+----------+ 1440
     K  N  L  S  L  D  E  E  A  S  K  W  N  K  V  L  T  D  K  N
     TTAAGCTCAACCGAGAAAGACAAGAAAATTTCCTCCTTACTTGAAGATAAGAACTATGAA
1441 ------------+----------+----------+----------+----------+ 1500
     L  S  S  T  E  K  D  K  K  I  S  S  L  L  E  D  K  N  Y  E
     GTTTATAAGAAACAATTTTATATCCTCAAAGATTTGCTTGTAGAACACTTTAACAAAATT
1501 ------------+----------+----------+----------+----------+ 1560
     V  Y  K  K  Q  F  Y  I  L  K  D  L  L  V  E  H  F  N  K  I
     GGGGAGCAGATTGCTAAAGATTATATGAAATAA
1561 ------------+----------+---- 1593
     G  E  Q  I  A  K  D  Y  M  K  *
```

METHOD OF CLONING AND EXPRESSION OF BSMBI RESTRICTION ENDONUCLEASE AND BSMBI METHYLASE IN *E. COLI* AND PURIFICATION OF BSMBI ENDONUCLEASE

BACKGROUND OF THE INVENTION

The present invention relates to recombinant DNA which encodes the BsmBI restriction endonuclease (endonuclease) as well as the BsmBI methyltransferase (methylase), expression of BsmBI endonuclease and methylase in *E. coli* cells containing the recombinant DNA.

BsmBI endonuclease is found in the strain of *Bacillus stearothermophilus* B61 (New England Biolabs' strain collection #857). It recognizes the double-stranded DNA sequence 5'CGTCTC3'$N_1$/$N_5$ (SEQ ID NO:1) and cleaves at $N_1$ (top strand) and $N_5$ (bottom strand) downstream of the recognition sequence to generate a 4-base 5' overhang (N=A, T, C, or G;/indicates the cleavage of phosphodiester bond). BsmBI methylase (M.BsmBI) is also found in the strain of *Bacillus stearothermophilus* B61. It recognizes the double-stranded DNA sequences 5'CGTCTC3' (SEQ ID NO:2) (top strand) and 5'GAGACG3' (SEQ ID NO:3) (bottom strand) and probably modifies a cytosine (5 mC) on the top strand and an adenosine (N6mA) on the bottom strand within the recognition sequences.

Type II restriction endonucleases are a class of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind particular sequences of nucleotides (the 'recognition sequence') along the DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, Nucl. Acids Res. 27:312–313, (1999)).

Restriction endonucleases typically are named according to the bacteria from which they are discovered. Thus, the species *Deinococcus radiophilus* for example, produces three different restriction endonucleases, named DraI, DraII and DraIII. These enzymes recognize and cleave the sequences 5'TTT/AAA3' (SEQ ID NO:4), 5'PuG/GNCCPy3' (SEQ ID NO:5) and 5'CACNNN/GTG3' (SEQ ID NO:6) respectively. *Escherichia coli* RY13, on the other hand, produces only one enzyme, EcoRI, which recognizes the sequence 5'G/AATTC3' (SEQ ID NO:7).

A second component of bacterial/viral restriction-modification (R-M) systems are the methylase. These enzymes co-exist with restriction endonucleases and they provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, $N_4$ methyl cytosine, or $N_6$ methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiably foreign DNA, is sensitive to restriction endonuclease recognition and cleavage. During and after DNA replication, usually the hemi-methylated DNA (DNA methylated on one strand) is also resistant to the cognate restriction digestion.

With the advancement of recombinant DNA technology, it is now possible to clone genes and overproduce the enzymes in large quantities. The key to isolating clones of restriction endonuclease genes is to develop an efficient method to identify such clones within genomic DNA libraries, i.e. populations of clones derived by 'shotgun' procedures, when they occur at frequencies as low as $10^{-3}$ to $10^{-4}$. Preferably, the method should be selective, such that the unwanted clones with non-methylase inserts are destroyed while the desirable rare clones survive.

A large number of type II restriction-modification systems have been cloned. The first cloning method used bacteriophage infection as a means of identifying or selecting restriction endonuclease clones (EcoRII: Kosykh et al., Mol. Gen. Genet. 178:717–719, (1980); HhaII: Mann et al., Gene 3:97–112, (1978); PstI: Walder et al., Proc. Nat. Acad. Sci. 78:1503–1507, (1981)). Since the expression of restriction-modification systems in bacteria enables them to resist infection by bacteriophages, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into *E. coli* cloning vectors (EcoRV: Bougueleret et al., Nucl. Acids. Res. 12:3659–3676, (1984); PaeR7: Gingeras and Brooks, Proc. Natl. Acad. Sci. USA 80:402–406, (1983); Theriault and Roy, Gene 19:355–359 (1982); PvuII: Blumenthal et al., J. Bacteriol. 164:501–509, (1985); Tsp45I: Wayne et al. Gene 202:83–88, (1997)).

A third approach is to select for active expression of methylase genes (methylase selection) (U.S. Pat. No. 5,200,333 and BsuRI: Kiss et al., Nucl. Acids. Res. 13:6403–6421, (1985)). Since restriction-modification genes are often closely linked together, both genes can often be cloned simultaneously. This selection does not always yield a complete restriction system however, but instead yields only the methylase gene (BspRI: Szomolanyi et al., Gene 10:219–225, (1980); BcnI: Janulaitis et al., Gene 20:197–204 (1982); BsuRI: Kiss and Baldauf, Gene 21:111–119, (1983); and MspI: Walder et al., J. Biol. Chem. 258:1235–1241, (1983)).

A more recent method, the "endo-blue method", has been described for direct cloning of thermostable restriction endonuclease genes into *E. coli* based on the indicator strain of *E. coli* containing the dinD::lacz fusion (U.S. Pat. No. 5,498,535, (1996); Fomenkov et al., Nucl. Acids Res. 22:2399–2403, (1994)). This method utilizes the *E. coli* SOS response signals following DNA damage caused by restriction endonucleases or non-specific nucleases. A number of thermostable nuclease genes (TaqI, Tth111I, BsoBI, Tf nuclease) have been cloned by this method (U.S. Pat. No. 5,498,535, 1996). The disadvantage of this method is that some positive blue clones containing a restriction endonuclease gene are difficult to culture due to the lack of the cognate methylase gene.

There are three major groups of DNA methyltransferases based on the position and the base that is modified (C5 cytosine methylases, N4 cytosine methylases, and N6 adenine methylases). N4 cytosine and N6 adenine methylases are amino-methyltransferases (Malone et al. J. Mol. Biol. 253:618–632, (1995)). When a restriction site on DNA is modified (methylated) by the methylase, it is resistant to digestion by the cognate restriction endonuclease. Sometimes methylation by a non-cognate methylase can also confer the DNA site resistant to restriction digestion. For example, Dcm methylase modification of 5'CCWGG3' (SEQ ID NO:8) (W=A or T) can also make the DNA resistant to PspGI restriction digestion. Another example is that CpM methylase can modify the CG dinucloetide and make the NotI site (5'GCGGCCGC3' (SEQ ID NO:9)) refractory to NotI digestion (New England Biolabs' Catalog, 2000–01, page 220). Therefore methylases can be used as a tool to modify certain DNA sequences and make them uncleavable by restriction enzymes.

Because purified restriction endonucleases and modification methylases are useful tools for creating recombinant molecules in the laboratory, there is a strong commercial interest to obtain bacterial strains through recombinant DNA techniques that produce large quantities of restriction enzymes. Such over-expression strains should also simplify the task of enzyme purification.

SUMMARY OF THE INVENTION

The present invention relates to a method for cloning the BsmBI restriction endonuclease from Bacillus stearothermophilus B61 into *E. coli* by methylase selection and inverse PCR. A methylase gene with high homology to $C_5$ methylase was found in a DNA library after methylase selection. A second methylase gene with high homology to amino-methylases ($N_6$-adenosine methylases) was found after sequencing the genomic DNA surrounding the first methylase gene. It was later determined that these two genes are fused together and code for a single fusion protein. This fusion gene was named BsmBI methylase gene (bsmBIM). The bsmBIM gene was amplified by PCR and cloned into pACYC184. The premodified host ER2744 [pACYC-BsmBIM] was used for BsmBI endonuclease expression.

It proved to be difficult to express BsmBI endonuclease in medium-copy-number expression vectors. When PCR DNA containing bsmBIR gene was ligated to pAII17 or pET21at, no active clones with correct insert were found, which may be due to under-methylation of BsmBI sites in *E. coli* genome or the vectors.

In order to construct a stable expression clone, the bsmBIM gene was amplified by PCR and cloned into pBR322, giving rise to pre-modified host ER2744 [pBR322-BsmBIM]. The bsmBIR gene was amplified by PCR and inserted into pACYC-T7ter with compatible ends. High BsmBI endonuclease activity was detected. However, the expression clone ER2744 [pBR-BsmBIM, pACYC-T7ter-BsmBIR] was not very stable because lower BsmBI activity was detected in larger amplified cultures. To further stabilize the expression clone, two strategies were used:
 a. Introducing another plasmid carrying the T7 lysS gene coding for T7 lysozyme which inhibits T7 RNA polymerase and thus reduces the constitutive expression from the T7 promoter.
 b. Using a non-cognate methylase BsmAI methylase to premodify the expression host (BsmAI methylase recognition sequence 5'GTCTC3' $N_1/N_5$ (SEQ ID NO:27).

Two production strains were constructed. The first one was ER2566 [pBR322-BsmBIM, pCEF8, pACYC-T7ter-BsmBIR]. The second strain was a pre-modified strain by a non-cognate methylase, BsmAI methylase, ER2566 [pBR322-BsmAIM, pACYC-T7ter-BsmBIR]. This second strain generated the highest BsmBI production yield in amplified large cultures.

BRIEF DESCRIPTION OF THE DRAWINGS

FIG. 2. DNA sequence (SEQ ID NO:10) of BsmBI methylase gene (bsmBIM, 3207 bp) and its encoded amino acid sequence (SEQ ID NO:11).

FIG. 3. DNA sequence (SEQ ID NO:12) of BsmBI endonuclease gene (bsmBIR, 1593 bp) and its encoded amino acid sequence (SEQ ID NO:13).

DETAILED DESCRIPTION OF THE INVENTION

Figure 1:
FIG. 1. Gene organization of BsmBI restriction-modification system. bsmBIR, BsmBI restriction endonuclease gene; bsmBIM, BsmBI methylase gene.
Figure 4:
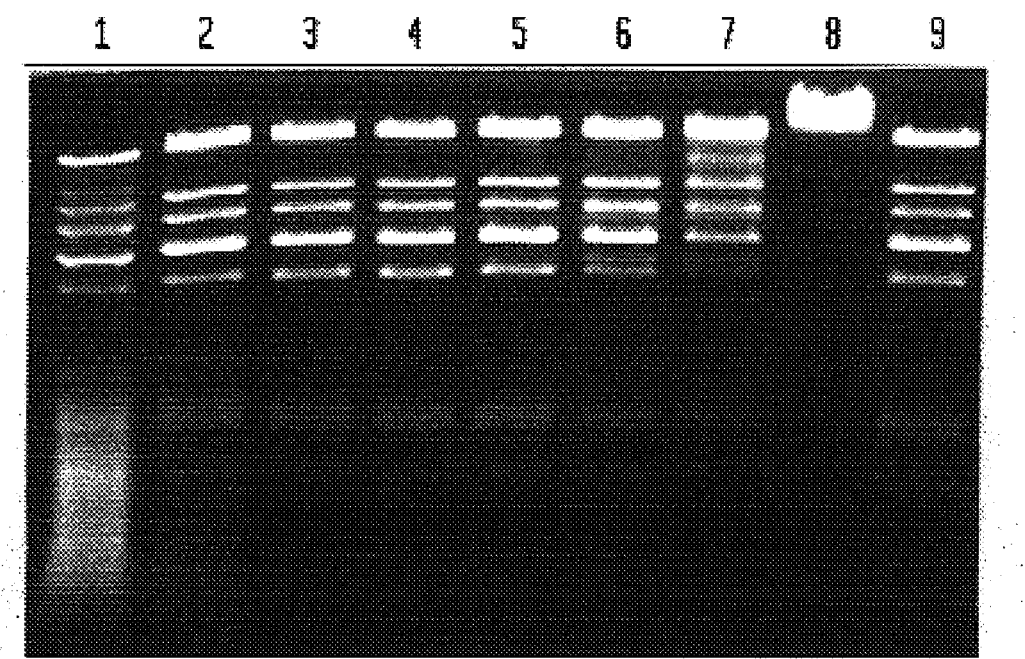
FIG. 4. Recombinant BsmBI endonuclease activity in cell extract. Lanes 1–7, λ DNA treated with cell extract containing recombinant BsmBI restriction endonuclease; The dilution factors in lanes 1–7: 1×, 1:10, 1:100, 1:1000, 1:2000, 1:3000, 1:4000. Lane 8, λ DNA; lane 9, λ DNA digested with purified native BsmBI.

The bsmBIM gene was first cloned by methylase selection. After the entire gene was sequenced, it was amplified from the genomic DNA by PCR. Following digestion with BamHI and SalI, the PCR DNA was ligated to pACYC184. Five clones containing the plasmid pACYC184-BsmBIM showed full resistance to BsmBI cleavage. Competent cells ER2744 [pACYC-BsmBIM] was prepared and used for BsmBI endonuclease expression.

It proved to be difficult to express BsmBI endonuclease in medium-copy-number expression vectors. The bsmBIR gene was amplified by PCR and digested with NdeI and BamHI overnight. After DNA purification, the PCR DNA was ligated into pA1117 with compatible ends. The ligated DNA was transformed into premodified host ER2744 [pACYC-BsmBIM] and selected for $Ap^R$ $Cm^R$ transformants. Mini-preparations from a large number of transformants did not identify positive clones with the correct size insert. It was concluded that it was difficult to clone and express bsmBIR gene in the medium-copy-number plasmid pAII17 with ColEI origin.

The remaining purified PCR products of the bsmBIR gene were digested with NdeI and BamHI. After purification, the PCR DNA was ligated into pET21at with compatible ends. The ligated DNA was transformed into pre-modified host ER2744 [pACYC-BsmBIM] and selected for $Ap^R$ $Cm^R$ transformants. Again a large number of transformants were screened for insert. No clones carrying the desired insert were found. The bsmBIR gene seemed to be toxic when it was expressed from a medium-copy-number plasmid (either pAII17 or pET21at), which may be due to under-methylation of BsmBI sites in *E. coli* genome or the vectors.

Another expression strategy which alternatively proved to be successful comprised the expression of BsmBI endonuclease gene in which the methylase gene was expressed in pBR322 and the endonuclease gene was expressed in pACYC-T7ter. The plasmid pACYC-T7ter contained a T7 promoter, p15A replication origin (low-copy-number, 5–8 copies per cell), and four copies of transcription terminators upstream of T7 promoter.

The method described herein by which the BsmBI methylase gene and the BsmBI restriction endonuclease genes are preferably cloned and expressed in *E. coli* using the following steps:

1. Construction of ApoI, NlaIII, and Sau3AI Partial Genomic DNA Libraries

NlaIII and Sau3AI genomic libraries were constructed using the vector pUC19. The NlaIII and Sau3AI genomic libraries were challenged with BsmBI and the resistant circular DNA was used to transform ER2502 competent cells. Plasmid DNA was prepared from the transformants and screened for resistance to BsmBI digestion. Three clones were identified to be resistant to BsmBI digestion. The insert in one of the clones was sequenced and a fused methylase gene was found and named bsmBIM gene. A partial ORF was located downstream of the methylase gene.

2. Use of Inverse PCR to Amplify the bsmBIR Gene Sequence

To obtain the adjacent DNA sequence beyond bsmBIM gene, the genomic DNA was digested with AatII, AluI, BsaHI, BsaWI, BspHI, BsrGI, DraI, EcoRV, HindIII, Hyp94I, HpyCH4IV, PsiI, SspI, TaqI, TseI, and XbaI. The digested DNA was ligated and then used for inverse PCR amplification of bsmBIR gene. Inverse PCR products from AatII, HindIII, PsiI, and XbaI templates were gel-purified from low-melting agarose and directly sequenced. An ORF of 1593 bp was found downstream of the bsmBIM gene. This ORF was named bsmBIR gene. It encodes a 530-aa protein with predicted molecular mass of 62 kDa.

3. Cloning of bsmBIM into pBR322 to Construct a Premodified Host

In order to increase the BsmBI methylase expression in the expression host, bsmBIM PCR DNA was digested with BamHI and SalI was ligated into pBR322 with compatible ends. The ligated DNA was transformed into ER2566 competent cells. Three clones were identified to be fully resistant to BsmBI cleavage and had the correct insert size. The cells were then made competent by $CaCl_2$ treatment, resulting in a premodified host ER2566 [pBR322-BsmBIM].

4. Expression of bsmBIR Gene in T7 Expression Vector pACYC-T7ter

The bsmBIR gene was amplified by PCR and digested with BamHI. After DNA purification, the PCR DNA was ligated into pACYC-T7ter with compatible ends. The ligated DNA was transformed into pre-modified host ER2744 [pBR322-BsmBIM] and selected for $Ap^R$ $Cm^R$ transformants. ER2744 is an *E. coli* K strain derivative that carries the T7 RNA polymerase gene on chromosome (NEB strain collection). Nine clones were found to carry the desired insert. Cell extracts were prepared and assayed for BsmBI activity among the 9 clones. Two clones #24 and #26 displayed high BsmBI activity. The expression clone ER2744 [pBR-BsmBIM, pACYC-T7ter-BsmBIR] was not stable because lower BsmBI activity was detected in larger amplified cultures. To further stabilize the expression clone, two strategies were used:

a. Introducing another plasmid carrying the T7 lysS gene coding for T7 lysozyme that inhibits T7 RNA polymerase and thus reduces the constitutive expression from the T7 promoter.

b. Using a non-cognate methylase BsmAI methylase to premodify the expression host.

5. Construction of ER2566 [pBR322-BsmBIM, pCEF8] Premodified Host

Competent cells ER2566 [pBR322-BsmBIM] was transformed with pCEF8 ($Km^R$). The plasmid pCEF8 carries pSC101 origin and lysS gene that encodes T7 lysozyme. $Ap^R$, $Km^R$ transformants were amplified and made competent by washing with cold $CaCl_2$. ER2566 is a T7 expression host that was derived from *E. coli* B strain. ER2566 also carries the T7 RNA polymerase gene on chromosome (NEB strain collection). To reduce the PCR mutation rate, the bsmBIR gene was re-amplified by PCR with 13 PCR cycles from genomic DNA and re-cloned into the expression vector pACYC-T7ter. The pre-modified host was ER2566 [pBR322-BsmBIM, pCEF8]. The bsmBIR endonuclease gene containing plasmid pACYC-T7ter-BsmBIR was found in plasmid mini-screening. IPTG-induced cell extracts were prepared from clones with the insert and assayed for BsmBI endonuclease activity.

6. Expression of BsmBI Endonuclease in BsmAI Methylase Premodified Host

The recognition sequence of BsmAI and BsmBI are 5'GTCTC3' $N_1/N_5$ (SEQ ID NO:27) and 5'CGTCTC3' $N_1/N_5$ (SEQ ID NO:1), respectively. BsmAI sites are a subset of BsmBI sites. Both BsmAI methylase and BsmBI methylase are fusion of two methylases ($N^6A$ methylase fused with $C_5$ methylase). Based on the amino acid sequence homology between BsmAI and BsmBI methylases and the similarity in DNA recognition sequences of the two methylases, it was predicted that BsmAI methylase might protect *E. coli* genomic DNA against BsmBI cleavage. The expression plasmid pACYC-T7ter-BsmBIR was transformed into ER2566 [pBR322-BsmAIM] (BsmAI, U.S. application Ser. No.: 09/957,005). Cell extract from the uninduced, induced, and induced/heated (at 55° C. and 65° C.) was assayed for BsmBI activity. Highest activity was detected in the extract from IPTG-induced culture and from the induced culture heated at 55° C. The yield was determined to be approximately >$10^6$ units/g wet cells.

Protein expression profile of the uninduced, induced, and induced heated (at 55° C. and 65° C.) was analyzed by SDS-PAGE. A protein band of ~60 kDa was detected in the induced culture extracts, but absent in the uninduced culture extract.

7. Purification of BsmBI Endonuclease to Homogeneity

Seventy-five grams of IPTG-induced cells ER2566 [pBR322-BsmAIM, pACYC-T7ter-BsmBIR] were lysed by sonication. The clarified cell extract was heated at 59–61° C. for 20 min. The heat-denatured proteins were removed by centrifugation. BsmBI endonuclease was purified to near homogeneity through Heparin Hyper D, Source Q15 HR, and Heparin 5PW columns using a Äkta® FPLC system. The purifed BsmBI endonuclease has an apparent molecular mass of ~60 kDa on SDS-PAGE in comparison with predicted size of 62 kDa.

The present invention is further illustrated by the following Example. The Example is provided to aid in the understanding of the invention and is not construed as a limitation thereof.

The references cited above and below are herein incorporated by reference.

EXAMPLE 1

Cloning of BsmBI Methylase and Restriction Endonuclease Genes in *E. coli*

1. Preparation of Genomic DNA

The genomic DNA from *Bacillus stearothermophilus* B61 (New England Biolabs collection NEB#857) was prepared by resuspending 9.2 g of cell paste in 50 ml of 25% sucrose, 50 mM Tris-HCl by gently shaking for 10 min. Cell lysis was completed by addition of six ml of freshly prepared 10 mg/ml lysozyme in 0.25 M Tris-HCl (pH 8.0) and incubated at room temperature for 1 hour. Five ml of 0.25 M EDTA (pH 8.0) were then added to the suspension followed slow mixing of the suspension with a clean pipet. The EDTA chelates divalent cations and inactives non-specific endo/exonucleases. The cell lysis was further improved by addition of SDS to 1% final concentration. Thirty-six ml of lysis buffer (1% Triton-X 100, 50 mM Tris-HCl (pH 8.0), 0.62 M EDTA) was added and mixed by gentle swirling. The viscous lysed cell suspension was extracted with 120 ml of equilibrated phenol and the aqueous phase was recovered and this step was repeated. The supernatant was diluted with the addition of 100 ml of TE buffer (10 mM Tris-HCl (pH 8), 1 mM EDTA) to reduce viscosity. This was followed by extraction with 220 ml phenol once and extraction with 200 ml of chloroform once, where the DNA was recovered after centrifugation to separate it from the chloroform. The supernatant was then dialyzed 4 times in 2–4 L of TE buffer at 4° C. RNase A (150 µl of 10 mg/ml stock) was added to the resulting 150 ml solution and the solution was incubated at 37° C. for 1 hour. The DNA was precipitated by the addition of $1/10^{th}$ volume 3M NaOAc and 1 volume of isopropanol and was then collected by centrifugation. The DNA pellet was air-dried for 30 min then resuspended in 20 ml TE buffer by gentle shaking for 30 min to a final concentration of approximately 250 µg/ml.

2. Partial Digestion of Genomic DNA

The purified DNA was cleaved with ApoI, NlaIII, and Sau3AI to achieve partial digestion as follows: Three 500 µl solutions were made of *Bacillus stearothermophilus* DNA at 100 µg/ml; one in NEBuffer 3+BSA (100 mM NaCl, 50 mM Tris-HCl, 10 mM $MgCl_2$, 1 mM DTT, 100 µg/ml BSA, pH 7.9 @ 25° C.), one in NEBuffer 4+BSA (50 mM K-acetate, 20 mM Tris-acetate, 10 mM Mg-acetate, 1 mM DTT, 100 µg/ml BSA, pH 7.9 @ 25° C.), and one in NEBuffer Sau3AI+BSA (100 mM NaCl, 10 mM Bis Tris Propane-HCl, 10 mM $MgCl_2$, 1 mM DTT, 100 µg/ml BSA, pH 7.0 @ 25° C.). Each solution was divided into one 200 µl aliquot and three, 100 µl aliquots. To each 200 µl tube was added 2 µl of the respective enzyme (8 units of ApoI, 20 units of NlaIII, and 8 units of Sau3AI) to achieve 1 unit of enzyme per 2.5 µg of DNA for both reactions with ApoI and Sau3AI, and 1 unit of enzyme per µg of DNA for the reaction with NlaIII. One hundred µl was taken from each 200 µl aliquot and added to the second aliquot of the same buffer to achieve 1 unit of enzyme per 5 µg of DNA for reactions with ApoI and Sau3AI and 1 unit of enzyme per 2 µg of DNA for the reaction with NlaIII, and so on, each succeeding tube receiving half of the previous amount of the appropriate enzyme. The ApoI tubes were incubated at 50° C. and the NlaIII and Sau3AI tubes were incubated at 37° C. for 1 hour and 5 µl from each tube was analyzed by agarose gel electrophoresis. This procedure was repeated for NlaIII, with the exception of diluting NlaIII four-fold prior to addition to the reaction mixture, resulting in 1 unit of enzyme per 4 µg of DNA in the first tube, 1 unit of enzyme per 8 µg of DNA in the second tube, and so on. The contents of tubes exhibiting limited digestion and moderate, but incomplete digestion were run on a 1% low-melting-point agarose gel for 2 hours. DNA fragments between approximately 1 kb to 8 kb were excised from the gel and weighed. To each band $1/10^{th}$ volume β-Agarase Buffer (10 mM Bis Tris-HCl pH 6.8, 1 mM $Na_2EDTA$) was added followed by incubation at 65° C. for 10 min. The agarose was digested with $1/100^{th}$ volume β-Agarase with incubation at 42° C. for 90 min. When placed on ice, the solutions appeared to become gelatinous. Therefore, the tubes were further incubated at 65° C. for 10 min and then at 42° C. for 5 min, followed by the addition of $1/100^{th}$ volume β-Agarase and incubation at 42° C. for 90 min. The DNA was precipitated by adding $1/10^{th}$ volume 3 M NaOAc, incubation on ice for 15 min, and addition of 2 volumes of ethanol overnight. The solution was then centrifuged, decanted, and the DNA pellet was resuspended in 20 µl TE and 1 µl from each was analyzed by agarose gel electrophoresis.

3. Construction of ApoI, NlaIII, and Sau3AI Partial and Complete Genomic DNA Libraries ApoI, NlaIII, and Sau3AI genomic libraries were constructed using the vector pUC19. About 0.5 µg (3 µl) of each ApoI, NlaIII, and Sau3AI partially digested *Bacillus stearothermophilus* DNA, as described above, was mixed with ~0.1 µg pUC19, which had been digested with EcoRI, SphI, and BamHI and CIP-treated, respectively. To each tube was added 5 µl 10× ligation buffer and 1 µl (400 units) T4 DNA ligase in a total volume of 50 µl. The reactions were incubated at 16° C. overnight. The T4 DNA ligase was heat-inactivated at 65° C. for 30 min and the contents of each tube were then drop-dialyzed in 2 L $dH_2O$ using Type VS 0.025 µm filter paper for 4 hours to reduce salt concentration, resulting in a final volume of approximately 75 µl each.

4. Selection of M.BsmBI by the Methylase Selection Method

For transformation experiment 2 µl from each of the dialyzed DNA libraries, as described above, was transformed into ER2502 by electroporation using a BioRad Gene Pulser with settings of a capacitance of 25 µF., a voltage of 2.5 kV, and a resistance of 200 Ω. LB broth (0.5 ml) was added to each tube and then incubated at 37° C. for 1 hour. The contents of each tube were spread on Ap plates and incubated at 37° C. overnight to select transformants of pUC19 with ApoI, NlaIII, and Sau3AI genomic fragment inserts.

Approximately 1,000 transformants were obtained for the NlaIII library, and approximately 900 transformants were obtained for the Sau3AI library. No $Ap^R$ transformants were obtained from the ApoI library transformation. The transformants from the NlaIII and Sau3AI libraries were pooled and each amplified in 1 liter of overnight LB+Ap cultures at 37° C. Plasmid DNA was prepared from the overnight cells by the Qiagen® Maxi column method. One, 2, 5, and 10 µl (~0.2 µg, 0.4 µg, 1 µg, 2 µg DNA) from each plasmid library were challenged with BsmBI overnight at 55° C. Following BsmBI digestion, 5 µl from each of the digestions was transformed back into 100 µl each of ER2502 and ER2683 competent cells by the standard method (mixing 100 µl competent cells and plasmid DNA, 30 min on ice, 5 min at 37° C., 5 min at room temperature, adding 100 µl SOB, incubating for 1 hour at 37° C.). The transformation products were grown on Ap plates at 37° C. overnight. Two ml of LB+Ap were inoculated with individual $Ap^R$ colonies (33 from ER2683 cells, 3 from ER2502 cells). From each plasmid mini-preparation, 1 µg (5 µl) was screened for resistance by incubation with 30 units (3 µl) BsmBI for 1 hour at 55° C. and analyzed by agarose gel electrophoresis. Three clones were identified to be resistant to BsmBI digestion. Of these three clones two were found to have inserts. The fully resistant clone (BsmBIM positive) was derived from NlaIII partial library. It was concluded that either the fragment contained the bsmBIM gene or pUC19 had lost its BsmBIM sites. (Later, when the insert was sequenced, it was confirmed that it encodes the BsmBI methylase and that the BsmBI sites in the vector were intact.

5. Sequencing of bsmBIM Gene

The bsmBIM gene was sequenced by insertion of priming sites of GPS™-1 genome priming system (New England Biolabs®) and primer walking. The bsmBIM gene is 3207 bp, encoding a 1068-aa fusion protein with predicted molecular mass of 122.4 kDa. Sequence comparison with other methylases in GenBank indicated that M.BsmBI is a fusion protein, the result of the fusion of an amino-methylase ($N_6A$ methylase) and a $C_5$-methylase. During the sequencing of the bsmBIM gene it was determined that the restriction gene (bsmBIR) was likely located downstream of the bsmBIM gene since a partial ORF (later determined to be 1587 bp) was located there. This was hypothesized because the restriction gene and modification genes in most restriction-modification systems found to date have been identified to be within a few hundred base pairs of each other.

6. Cloning of bsmBIM Gene into pACYC184 and pLG339 to Construct a Premodified Host Three primers were synthesised with the following sequences:

```
5'taaggatccggaggtaaataaatgaactccttatcactaaaagatgaa3'  (SEQ ID NO:14)
     (249-164)

5'atgaaagtcgacccccgtaattttacgggcttttttaaaa3' (SEQ ID NO:15)
     (249-165)

5'tatggatccggaggtaaataaatgaaagtaatactgaatgatttagaa3'(SEQ ID NO:16)
     (249-255)
```

The bsmBIM gene was successfully amplified from the genomic DNA by PCR using primers 246–164 and 249–165 under conditions of 95° C. 5 min for 1 cycle, 95° C. 1 min, 55° C. 1 min, 72° C. 5 min for 25 cycles with Vent DNA polymerase. The PCR DNA was purified through a Qiagen spin column, digested with BamHI and SalI, and was ligated to CIP treated pACYC184 and pLG339 with compatible ends with the goal of inserting the PCR DNA into the middle of the tetracycline (Tc) resistance gene.

Vector pACYC184 with the ligated bsmBIM gene was transformed using the standard method into *E. coli* ER2683 and plated on chloramphenicol (Cm) plates. The pLG339 with the ligated bsmBIM gene was transformed using the standard method into *E. coli* ER2502 and grown on kanamycin (Km) plates. Transformants were tested for Tc sensitivity on Cm+Tc plates and Km+Tc plates, respectively. Clones with inserts in the Tc resistance gene should show Tc sensitivity due to the insertion of the insert in the middle of the Tc resistance gene.

Purified bsmBIM PCR DNA was digested with BamHI and SalI and was ligated to CIP treated pACYC184 and pLG339 with compatible ends. The ligated pLG339-BsmBIM was transformed using the standard method into ER2502 and grown on Km plates. The ligated pACYC184-BsmBIM was transformed using the standard method into ER2502 and grown on Cm plates. Colonies from both the Km plates and Cm plates were then inoculated onto Km+Tc plates and Cm+Tc plates, respectively. Eighteen colonies from the Km+Tc plates and 18 colonies from the Cm+Tc plates that showed Tc sensitivity were inoculated into LB+Km and LB+Cm, respectively. Mini-preparation DNA from each of these cultures was digested with BsmBI to test for resistance to cleavage. Of the 18 clones containing the plasmid pLG339 (from Km-containing plates), 4 showed full resistance to cleavage, 3 showed partial resistance to cleavage and 11 showed no resistance to cleavage. Of the 18 clones containing the plasmid pACYC184 (from Cm-containing plates), 6 showed full resistance to cleavage, 4 showed partial resistance to cleavage, and 8 showed no resistance to cleavage.

Plasmids from five of the six pACYC184 clones that showed full resistance to cleavage were cut with BamHI and SalI to check the insert size. All five clones had an insert of approximately 3.2 kb, the size of the bsmBIM gene. It was concluded that these clones were M.BsmBI positive because they showed both full resistance to cleavage by BsmBI and an insert the size of the bsmbIM gene. Of these five M.BsmBI positive clones, mini-preparation DNA from four of them was transformed into ER2744 using the standard method and grown on Cm plates. The resulting transformants were grown in LB broth+Cm, centrifuged, and were made competent by a cold $CaCl_2$ treatment, resulting in a premodified host ER2744 [pACYC-BsmBIM].

7. Cloning of bsmBIR Gene by Inverse PCR and Sequencing of bsmBIR Gene.

Seven primers were synthesized with the following sequences:

```
5'cccataaagcccgcacttgccatg3'         (SEQ ID NO:17)
                                      (249-33)

5'tgacgatgattccaaattacttag3'         (SEQ ID NO:18)
                                      (249-34)

5'ctttccctaaagctacttaattgaact3'      (SEQ ID NO:19)
                                      (249-256)

5'ttataacaacaatacacaagctttccc3'      (SEQ ID NO:20)
                                      (249-257)

5'tcttacccccatccttcagacaaac3'        (SEQ ID NO:21)
                                      (250-55)

5'aagacccagggcgacatgacgataa3'        (SEQ ID NO:22)
                                      (250-56)

5'tgtatatggacatattggaaagat3'         (SEQ ID NO:23)
                                      (250-57)
```

The genomic DNA was digested with AatII, AluI, BsaHI, BsaWI, BspHI, BsrGI, DraI, EcoRV, HindIII, Hyp94I, HpyCH4IV, PsiI, SspI, TaqI, TseI, and XbaI. The digested DNA was ligated at a low DNA concentration at 2 μg/ml and then used for inverse PCR amplification of bsmBIR gene using primers 249-33 and 249-34. Inverse PCR conditions were 94° C. 1 min, 55° C. 1 min, 72° C. 1 min for 35 cycles. Inverse PCR products were derived from AatII, AluI, BsrGI, DraI, HindIII, PsiI, TaqI, and XbaI templates. Inverse PCR products from AatII, HindIII, PsiI, and XbaI templates were gel-purified from low-melting agarose and sequenced using primers 249-33 and 249-34. Further sequencing of the PsiI and XbaI fragments was performed using primers 249-223 and 229-224. PCR was then performed using genomic DNA and primers 249-33 and 249-256 as well as with primers 249-33 and 249-257 under conditions of 94° C. 5 min for 1 cycle, 94° C. 1 min, 55° C. 1 min, 72° C. 2 min for 25 cycles. PCR products were gel-purified from low-melting agarose and sequenced using primers 249-33, 250-55, 250-56, and 250-57. An ORF of 1547 bp was found downstream of the bsmBIM gene. This ORF was named bsmBIR gene. It encodes a 530-aa protein with predicted molecular mass of 62 kDa.

8. Expression of bsmBIR Gene in T7 Expression Vector pAII17

Two primers were synthesized with the following sequence:

(SEQ ID NO:24)
5'gggtagatt<u>catatg</u>gctaaatacggacgtggaaagttt3'
(250—88)

(SEQ ID NO:25)
5'gct<u>ggatcc</u>tcatataatctttagcaatctgctccc3'
(250—89)

The bsmBIR gene was amplified by PCR using Vent DNA polymerase and primers 250-88 and 250-89 under conditions of 95° C. 2 min for 1 cycle, 95° C. 1 min, 60° C. 1 min, 72° C. 2 min for 20 cycles. The PCR products were purified by Qiagen spin column and digested with NdeI and BamHI overnight. After DNA purification, the PCR DNA was ligated into pAII17 with compatible ends. The ligated DNA was transformed into premodified host ER2744 [pACYC-BsmBIM] and selected for $Ap^R$ $Cm^R$ transformants. Among 54 plasmid mini-preparations, no clones carried the desired insert. It was concluded that it was difficult to clone and express bsmBIR gene in a medium-copy-number plasmid 9. Expression of bsmBIR Gene in T7 Expression Vector pET21at The remaining purified PCR products of the bsmBIR gene were digested with NdeI and BamHI. After DNA purification, the PCR DNA was ligated into pET21at with compatible ends. The ligated DNA was transformed into premodified host ER2744 [pACYC-BsmBIM] and selected for $Ap^R$ $Cm^R$ transformants. Among 36 plasmid screened, no clones carried the desired insert.

The bsmBIR gene amplification by PCR was repeated using Vent DNA polymerase and primers 250-88 and 250-89 under conditions of 95° C. 2 min for 1 cycle, 95° C. 1 min, 60° C. 1 min, 72° C. 2 min for 20 cycles. The PCR products were purified by phenol-CHCl₃ extraction and digested with NdeI and BamHI. After DNA purification, the PCR DNA was ligated into pET21at with compatible ends. The ligated DNA was transformed into premodified host ER2744 [pACYC-BsmBIM] and selected for $Ap^R$ $Cm^R$ transformants. Among 22 plasmid mini-preparations, no clones carried the desired insert. It was concluded that it's difficult to clone the bsmBIR gene in the pET vector probably as the result of under-methylation of BsmBI sites in the *E. coli* genome or the vector.

10. Cloning of bsmBIM into pBR322 to Construct a Premodified Host

The next expression strategy was to express bsmBIM gene in a medium-copy-number plasmid and to express bsmBIR gene in a low-copy-number plasmid. In order to increase the BsmBI methylase expression in the expression host, bsmBIM PCR DNA digested with BamHI and SalI was ligated into pBR322 with compatible ends. The ligated DNA was transformed into competent ER2566 and competent ER2683 and grown on ampicillin plates. Among 18 plasmid mini-preparations, 3 clones were fully resistant to BsmBI cleavage and had the correct insert size. The cells were then made competent by a cold CaCl₂ treatment, resulting in a pre-modified host ER2566 [pBR322-BsmBIM].

11. Expression of bsmBIR Gene in T7 Expression Vector pACYC-T7ter

One primer was synthesized with the following sequence:

(SEQ ID NO:26)
5'aag<u>ggatcc</u>ggaggtaaataaatggctaaatacggaaagttt3'
(252—270)

The bsmBIR gene was amplified by PCR using Vent DNA polymerase and primers 252-70 and 250-89 under conditions of 95° C. 2 min for 1 cycle, 95° C. 1 min, 60° C. 1 min, 72° C. 2 min for 20 cycles. The PCR products were purified by phenol-CHCl₃ extraction and digested with BamHI. After DNA purification, the PCR DNA was ligated into pACYC-T7ter with compatible ends. The ligated DNA was transformed into premodified host ER2744 [pBR322-BsmBIM] and selected for $Ap^R$ $Cm^R$ transformants. Among 72 plasmid mini-preparations, 9 clones carried the desired insert. All 9 clones were cultured in 10 ml LB plus Ap and Cm and induced with IPTG (0.5 mM final) for 3 h. Cell extracts were prepared and assayed for BsmBI activity. Two clones #24 and #26 displayed high BsmBI activity. These two clones were cultured in 500 ml LB plus Ap and Cm and induced with IPTG (0.5 mM final) for 3 h. Both clones #24 and #26 showed high BsmBI activity. More than $10^6$ units per gram of wet cells were found. BsmBI displays the highest specific activity among the type IIs restriction enzymes. The clones #24 and #26 were each grown in 20 ml LB plus Ap and Cm, and 10 ml from each were induced with IPTG (0.5 mM final) for 3 h. One ml from each induced culture was then split into three equal aliquots; one left unheated, one heated for 45 min at 55° C., and one heated for 45 min at 65° C. In both clones, all three induced culture aliquots and the uninduced culture showed activity. Five, 10, and 15 µl from each of the four samples from both clones were analyzed by polyacrylamide gel electrophoresis. It was determined from the gel that a protein of the approximate size of BsmBI (~60 kDa) was present in the induced samples.

Clone #24 was inoculated into 500 ml LB+Ap+Cm, grown overnight at 37° C. Ten ml of the overnight cells were used to inoculate a fresh 500 ml LB+Ap+Cm, grown at 37° C. for 4 h, induced with IPTG (0.5 mM final) for 3 h. Cells were harvested and assayed for BsmBI activity. The extract showed activity characteristic of BsmBI endonuclease cleavage, but the yield was much lower than small 10 ml culture that grown from fresh transformants. It was concluded that the expression clone ER2744 [pBR322-BsmBIM, pACYC-T7ter-BsmBIR] was not a very stable clone. To further stabilize the expression clone, two strategies were used:

a. Introducing another plasmid carrying the T7 lysS gene coding for T7 lysozyme that inhibits T7 RNA polymerase and thus reduces the constitutive expression from the T7 promoter.

b. Using a non-cognate methylase BsmAI methylase to premodify the expression host.

12. Construction of ER2566 [pBR322-BsmBIM, pCEF8] Premodified Host

The plasmid pCEF8 carries pSC101 replication origin and lysS gene that encodes the T7 lysozyme. Plasmid pCEF8 is compatible with pBR322 and pACYC-T7ter and therefore it can be transformed into the same expression host. Competent cells ER2566 [pBR322-BsmBIM] (100 µl) was transformed with 10 µl of pCEF8 ($Km^R$) by the standard method and grown on Ap+Km plates overnight at 37° C. $Ap^R$, $Km^R$ transformants were inoculated into eight 10 ml LB Ap+Km tubes, grown for 2.5 hours at 37° C., and made competent by washing with cold $CaCl_2$.

13. Expression of bsmBIR Gene in T7 Expression Vector pACYC-T7ter and in the Presence of LysS PCR was performed to amplify the bsmBIR gene using primers 252-270 and 249-89 under conditions of 1 cycle of 95° C. for 2 min and 13 cycles of 95° C. for 1 min, 60° C. for 1 min, and 72° C. for 2 min. The low PCR cycles (13 cycles) was intended to reduce mutation rate in PCR. PCR DNA was extracted twice with an equal volume phenol-chloroform, extracted once with equal volume chloroform, precipitated with NaOAc, cold 95% ethanol and washed with cold 70% ethanol. The purified PCR DNA was then digested with BamHI at 37° C. overnight, 0.5 µg from which was used in a ligation with 0.1 µg pACYC-T7ter in ligation buffer overnight at 16° C.

Ligated plasmid DNA (5 µl) was transformed into 100 µl ER2566 [pBR322-BsmBIM, pCEF8] and grown at 37° C. overnight on LB+Ap+Cm+Km plates. Thirty-six $Ap^R$, $Cm^R$, $Km^R$ transformants were each inoculated into 2 ml LB+Ap+Cm+Km and grown overnight at 37° C. BamHI digestion of mini-preparation DNA from the 36 clones revealed that 24 clones contained an insert of the correct size (approximately 1.5 kb). Digestion with NdeI and BamHI of the mini-preparation DNA from the 24 clones revealed that 15 of these clones had the bsmBIR gene in the correct orientation. The remaining cultures from these 15 clones were inoculated into 10 ml LB+Ap+Cm+Km, grown at 37° C. for 4 hours, centrifuged at 6 k rpm for 10 min, resuspended in 1 ml sonication buffer, sonicated twice for 30 sec, and centrifuged at 14 k rpm for 10 min. The resulting supernatant was assayed for activity, revealing BsmBI-like activity in 13 of the clones. This new expression strain contained three plasmids, ER2566 [pBR322-BsmBIM, pCEF8, pACYC-T7ter-BsmBIR]. One silent mutation was found in the bsmBIR gene in pACYC-T7ter-BsmBIR. The entire gene was sequenced to ensure that it encodes the wild type amino acid sequence.

14. Expression of BsmBI Endonuclease in BsmAI Premodified Host

Mini-preparation DNA from two clones (#1 and #10) was transformed into ER2566 [pBR322-BsmAIM] (BsmAI, Z.y.Zhu, J. Zhou, S. -y.Xu, USA patent pending) and grown overnight at 30° C. on LB+Ap+Cm plates. The colony from each clone was inoculated into 2.5 ml LB+Ap+Cm and grown overnight at 30° C. Each of these were then inoculated into 10 ml LB+Ap+Cm, grown for 4 hours at 30° C., induced with 0.5 mM IPTG, and grown for another 3 hours at 30° C. The cells were centrifuged at 12 k rpm for 10 min, resuspended in 1 ml sonication buffer, and assayed for BsmBI activity. The highest activity was detected in ER2566 [pBR322-BsmAIM pACYC-T7ter-BsmBIR] from the three cultures with clone #10 (10A, 10B, and 10C). Clone #10B, ER2566 [pBR322-BsmAIM, pACYC-T7ter-BsmBIR], was inoculated into two 500 ml LB+Ap+Cm, grown for 7 hours at 30° C., with one of the cultures being induced with 0.5 mM IPTG after 4 hours. Cells were centrifuged at 6 k rpm for 10 min and weighed (1.63 g). Cells from each culture were resuspended in 16 ml sonication buffer, sonicated for 10 min, and centrifuged at 14 k rpm for 12 min at 4° C. From the induced culture, 1 ml was heated at 55° C. for 40 min and 1 ml was heated at 65° C. for 40 min, both followed by centrifugation at 14 k rpm for 10 min at 4° C. Cell extracts from the uninduced, induced, and induced heated (both at 55° C. and 65° C.) were assayed for BsmBI activity and the results were analyzed by agarose gel electrophoresis. Highest activity was seen in the extract from the induced culture and from the induced culture heated at 55° C. From the activity of the induced clone and the induced clone heated at 55° C., it was determined that the cells contained approximately >$10^6$ units/g cells.

Protein expression profiles of the uninduced, induced, and induced heated (both at 55° C. and 65° C.) was analyzed by SDS-PAGE. A protein band at approximately 60 kDa (the size of BsmBI endonuclease) was detected in the induced culture extracts, but absent in the uninduced culture extract.

15. Purification of BsmBI Endonuclease to Homogeneity

Seventy-five grams of IPTG-induced cells ER2566 [pBR322-BsmAIM, pACYC-T7ter-BsmBIR] were resuspended in 260 ml Buffer A (0.1 M NaCl, 20 mM $KPO_4$, 0.1 mM EDTA, 10 mM β-mercaptoethanol) by gentle pipeting and swirling. The cell suspensions were sonicated for 2 min intervals and protein concentration was estimated using a Bradford assay after each interval. After 6 sonication intervals the cells were centrifuged for 1 hour at 12 k rpm. The resulting supernatant was then heated at 59–61° C. for 20 min. The heat-treated solution was then centrifuged for 30 min at 12 k rpm to remove denatured proteins. A 255 ml Heparin Hyper D column was equilibrated with 4 column volumes of Buffer A. 25 ml fractions were eluted with a NaCl gradient of 0.1 M to 1.0 M using a Äkta® FPLC. Äkta® recorded UV spectroscopy of the fractions revealed two peaks that were eluted at approximately 0.73 and 0.85 M NaCl, respectively. An activity assay of the fraction contents revealed that activity coincided with the second peak on the chromatogram. Protein composition as analyzed by SDS-PAGE showed a distinct difference in the protein of the first and second chromatogram peaks. Eight fractions (200 ml) were pooled and diluted with 1.1 L Buffer C (20 mM Tris-HCl, 0.1 mM EDTA, 10 mM β-mercaptoethanol, pH 7.8) due to the high salt concentration.

A 7.1 ml Source Q15 HR column was equilibrated with 3 column volumes of Buffer A2 (0.1 M NaCl, 20 mM Tris-HCl, 0.1 mM EDTA, 10 mM β-mercaptoethanol). One ml fractions were eluted with a NaCl gradient of 0.1 M to 1.0 M using a Äkta® FPLC. UV chromatogram showed only minor peaks in the gradient fractions. A Bradford assay and activity assay analyzed by agarose gel electrophoresis revealed that the enzyme was in the flow-through of the column. The wash and the flow-through were pooled.

Figure 5:
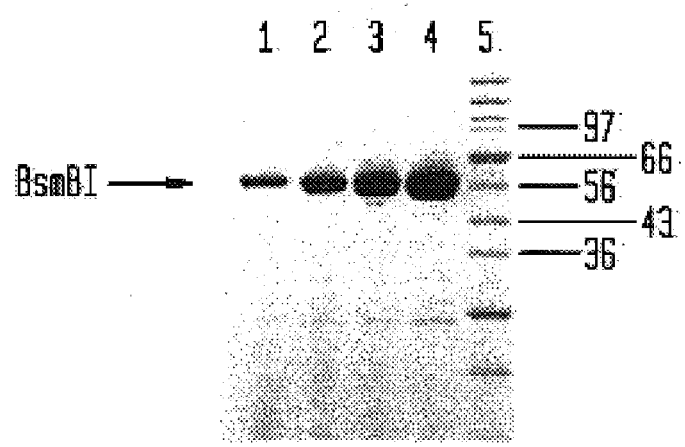
FIG. 5. Purified recombinant BsmBI endonuclease. Lanes 1–4, 1 μl, 3 μl, 5 μl, and 10 μl of purified BsmBI endonuclease after purification through Heparin 5PW column; lane 5, protein size marker. The predicted size of BsmBI endonuclease is 62 kDa. The apparent size of BsmBI endonuclease on the SDS-PAG gel is ~60 kDa.

A 7.1 ml Heparin 5PW column was equilibrated with 3 column volumes of Buffer A. One ml fractions were eluted with a NaCl gradient of 0.1 M to 1.0 M using a Äkta® FPLC. Data obtained from the chromatogram, SDS-PAGE, and an activity assay analyzed by agarose gel electrophoresis revealed that the one major peak seen on the chromatogram corresponded to the BsmBI endonuclease. Eight 1 ml fractions were pooled and dialyzed by 1 L of dialysis buffer (50 mM KCl, 10 mM Tris-HCl, 0.1 mM EDTA, 1 mM DTT, 5 mM β-mercaptoethanol, 50% glycerol, pH 7.5). The final purified BsmBI endonuclease protein was shown in FIG. 5.

The strain ET2566 [pBR322-BsmAIM, pACYC-T7ter-BsmBIR] has been deposited under the terms and conditions of the Budapest Treaty with the American Type Culture Collection on Sep. 28, 2001 and received ATCC Accession No. PTA-3739.

What is claimed is:

1. Isolated DNA coding for the BsmBI restriction endonuclease, wherein the isolated DNA is obtainable from *Bacillus stearothermophilus* B61.

2. A recombinant DNA vector comprising a vector into which a DNA segment encoding the BsmBI restriction endonuclease has been inserted.

3. Isolated DNA encoding the BsmBI restriction endonuclease wherein the isolated DNA is obtainable from ATCC Accession No. PTA-3739.

4. A vector which comprises the isolated DNA of claim 3.

5. A host cell transformed by the vector of claim 2 or 4.

6. A method of producing recombinant BsmBI restriction endonuclease comprising culturing a host cell transformed with the vector of claim 2 or 4 under conditions suitable for expression of said endonuclease and methylase.

* * * * *

SEQUENCE LISTING

<160> NUMBER OF SEQ ID NOS: 27

<210> SEQ ID NO 1
<211> LENGTH: 6
<212> TYPE: DNA
<213> ORGANISM: Bacillus stearothermophilus B61

<400> SEQUENCE: 1 cgtctc     6

<210> SEQ ID NO 2
<211> LENGTH: 6
<212> TYPE: DNA
<213> ORGANISM: Bacillus stearothermophilus B61

<400> SEQUENCE: 2 cgtctc     6

<210> SEQ ID NO 3
<211> LENGTH: 6
<212> TYPE: DNA
<213> ORGANISM: Bacillus stearothermophilus B61

<400> SEQUENCE: 3 gagacg     6

<210> SEQ ID NO 4
<211> LENGTH: 6
<212> TYPE: DNA
<213> ORGANISM: Deinococcus radiophilus

<400> SEQUENCE: 4 tttaaa     6

<210> SEQ ID NO 5
<211> LENGTH: 5
<212> TYPE: DNA
<213> ORGANISM: Deinococcus radiophilus
<220> FEATURE:
<223> OTHER INFORMATION: N=G, A, C or T

<400> SEQUENCE: 5 ggncc     5

<210> SEQ ID NO 6
<211> LENGTH: 9
<212> TYPE: DNA
<213> ORGANISM: Deinococcus radiophilus
<220> FEATURE:
<223> OTHER INFORMATION: N=G, A, C or T

<400> SEQUENCE: 6 cacnnngtg     9

<210> SEQ ID NO 7
<211> LENGTH: 6
<212> TYPE: DNA
<213> ORGANISM: Escherichia coli RY13

<400> SEQUENCE: 7 gaattc     6

-continued

```
<210> SEQ ID NO 8
<211> LENGTH: 5
<212> TYPE: DNA
<213> ORGANISM: Escherichia coli
<220> FEATURE:
<223> OTHER INFORMATION: W=A or T

<400> SEQUENCE: 8 ccwgg                                                                      5

<210> SEQ ID NO 9
<211> LENGTH: 8
<212> TYPE: DNA
<213> ORGANISM: Nocardia otitidis-caviarum

<400> SEQUENCE: 9 gcggccgc                                                                   8

<210> SEQ ID NO 10
<211> LENGTH: 3207
<212> TYPE: DNA
<213> ORGANISM: Bacillus stearothermophilus B61
<220> FEATURE:
<221> NAME/KEY: CDS
<222> LOCATION: (1)..(3207)

<400> SEQUENCE: 10
```

| | | | | | | | | | | | | | | | | |
|---|---|---|---|---|---|---|---|---|---|---|---|---|---|---|---|---|
| atg | aac | tcc | tta | tca | cta | aaa | gat | gaa | atg | gag | att | tgg | aaa | caa | gct | 48 |
| Met | Asn | Ser | Leu | Ser | Leu | Lys | Asp | Glu | Met | Glu | Ile | Trp | Lys | Gln | Ala | |
| 1 | | | | 5 | | | | | 10 | | | | | 15 | | |
| tct | aat | att | cga | aaa | aaa | att | gca | atg | gaa | acg | gcg | gcg | gaa | ttt | tta | 96 |
| Ser | Asn | Ile | Arg | Lys | Lys | Ile | Ala | Met | Glu | Thr | Ala | Ala | Glu | Phe | Leu | |
| | | | 20 | | | | | 25 | | | | | 30 | | | |
| aat | gaa | ttt | aat | gct | gaa | aaa | gca | ctt | aag | caa | ata | aaa | aat | tca | att | 144 |
| Asn | Glu | Phe | Asn | Ala | Glu | Lys | Ala | Leu | Lys | Gln | Ile | Lys | Asn | Ser | Ile | |
| | | 35 | | | | | 40 | | | | | 45 | | | | |
| cta | aat | ccg | ctc | tat | gaa | agg | aat | cct | ttt | caa | aat | aca | ttg | gaa | aag | 192 |
| Leu | Asn | Pro | Leu | Tyr | Glu | Arg | Asn | Pro | Phe | Gln | Asn | Thr | Leu | Glu | Lys | |
| | 50 | | | | | 55 | | | | | 60 | | | | | |
| ctt | tct | ttc | tct | cta | tat | tta | aca | gaa | aaa | tct | ata | gat | tat | gtt | ctt | 240 |
| Leu | Ser | Phe | Ser | Leu | Tyr | Leu | Thr | Glu | Lys | Ser | Ile | Asp | Tyr | Val | Leu | |
| 65 | | | | | 70 | | | | | 75 | | | | | 80 | |
| caa | atg | gaa | gtg | gag | cct | ata | aag | aaa | tta | tca | tat | gcc | aat | ttt | ttt | 288 |
| Gln | Met | Glu | Val | Glu | Pro | Ile | Lys | Lys | Leu | Ser | Tyr | Ala | Asn | Phe | Phe | |
| | | | | 85 | | | | | 90 | | | | | 95 | | |
| gtt | gag | ata | gga | gca | agg | gag | ttt | atc | tca | cct | ttt | cat | cct | gat | aaa | 336 |
| Val | Glu | Ile | Gly | Ala | Arg | Glu | Phe | Ile | Ser | Pro | Phe | His | Pro | Asp | Lys | |
| | | | 100 | | | | | 105 | | | | | 110 | | | |
| att | gag | aag | aat | tta | aca | gct | tca | aaa | gct | tat | gga | tat | ttt | ttc | aca | 384 |
| Ile | Glu | Lys | Asn | Leu | Thr | Ala | Ser | Lys | Ala | Tyr | Gly | Tyr | Phe | Phe | Thr | |
| | | 115 | | | | | 120 | | | | | 125 | | | | |
| cca | att | tca | tta | ggg | aca | aga | atg | gtt | aag | tta | gct | tta | aaa | gat | aaa | 432 |
| Pro | Ile | Ser | Leu | Gly | Thr | Arg | Met | Val | Lys | Leu | Ala | Leu | Lys | Asp | Lys | |
| | 130 | | | | | 135 | | | | | 140 | | | | | |
| cct | aaa | aat | cta | aaa | tct | ata | gtt | gac | cct | gcc | tgt | ggt | ata | ggc | agt | 480 |
| Pro | Lys | Asn | Leu | Lys | Ser | Ile | Val | Asp | Pro | Ala | Cys | Gly | Ile | Gly | Ser | |
| 145 | | | | | 150 | | | | | 155 | | | | | 160 | |
| tta | cta | gca | ttg | gct | cta | ata | tat | aat | cca | gaa | ata | gaa | aat | gtt | gta | 528 |
| Leu | Leu | Ala | Leu | Ala | Leu | Ile | Tyr | Asn | Pro | Glu | Ile | Glu | Asn | Val | Val | |
| | | | | 165 | | | | | 170 | | | | | 175 | | |
| gga | ata | gaa | ttg | gat | agc | ttt | acc | gct | aat | att | tcc | cat | aaa | tta | ctt | 576 |
| Gly | Ile | Glu | Leu | Asp | Ser | Phe | Thr | Ala | Asn | Ile | Ser | His | Lys | Leu | Leu | |
| | | | 180 | | | | | 185 | | | | | 190 | | | |

-continued

| | |
|---|---|
| gtt aga ata agt aaa gac tta gga ata aca cct aag att aag ata att<br>Val Arg Ile Ser Lys Asp Leu Gly Ile Thr Pro Lys Ile Lys Ile Ile<br>     195                    200                205 | 624 |
| aat caa aat ttc ttg gac tac gtt ttg aac tat gaa gaa gaa cat aag<br>Asn Gln Asn Phe Leu Asp Tyr Val Leu Asn Tyr Glu Glu Glu His Lys<br>210                   215                220 | 672 |
| gaa aag ttt gat ttg ctt att atg aat ccc cct tat gga agg gtg aga<br>Glu Lys Phe Asp Leu Leu Ile Met Asn Pro Pro Tyr Gly Arg Val Arg<br>225                230              235             240 | 720 |
| ttc ctg aaa aat tct tta act aat aaa gaa act aaa agt ggg ctt act<br>Phe Leu Lys Asn Ser Leu Thr Asn Lys Glu Thr Lys Ser Gly Leu Thr<br>           245                250             255 | 768 |
| gag gga atc tct gag tta gaa aaa aag ctt aga gaa gaa aca atc ctt<br>Glu Gly Ile Ser Glu Leu Glu Lys Lys Leu Arg Glu Glu Thr Ile Leu<br>260                   265                270 | 816 |
| aac gca gcg gat tta cgg aag aaa ttt gca tcg gtt gga ctt gga aag<br>Asn Ala Ala Asp Leu Arg Lys Lys Phe Ala Ser Val Gly Leu Gly Lys<br>           275                280             285 | 864 |
| ggg acc cct gaa tat tca aag gta ttc cta gct att tca aca aag ata<br>Gly Thr Pro Glu Tyr Ser Lys Val Phe Leu Ala Ile Ser Thr Lys Ile<br>290                   295                300 | 912 |
| gta aag caa aat ggt tat gtt att gca ata acc cca tca tca tgg tta<br>Val Lys Gln Asn Gly Tyr Val Ile Ala Ile Thr Pro Ser Ser Trp Leu<br>305                   310              315             320 | 960 |
| ggt gat gaa agt gga aga gaa cta aga aag tat tta gtt gag aat cat<br>Gly Asp Glu Ser Gly Arg Glu Leu Arg Lys Tyr Leu Val Glu Asn His<br>           325                330             335 | 1008 |
| gga atc tca tgt ata tgg aat ttt aaa gaa agt gct aaa tta ttt tca<br>Gly Ile Ser Cys Ile Trp Asn Phe Lys Glu Ser Ala Lys Leu Phe Ser<br>           340                345             350 | 1056 |
| ggt gtt aat caa cct aca acc gtt gta aaa att aaa gtt aat tca aat<br>Gly Val Asn Gln Pro Thr Thr Val Val Lys Ile Lys Val Asn Ser Asn<br>355                   360              365 | 1104 |
| gaa tca aag ata gaa att caa ggt cct cta tct tct cta gaa gaa cta<br>Glu Ser Lys Ile Glu Ile Gln Gly Pro Leu Ser Ser Leu Glu Glu Leu<br>370                   375              380 | 1152 |
| gga agg gat atc cag tat ttg gac aca tgt aat ata aaa aaa tac agt<br>Gly Arg Asp Ile Gln Tyr Leu Asp Thr Cys Asn Ile Lys Lys Tyr Ser<br>385                   390              395             400 | 1200 |
| cca gaa tgg tat aga ata ccc caa tgc ggg aat gag cga gca aaa ata<br>Pro Glu Trp Tyr Arg Ile Pro Gln Cys Gly Asn Glu Arg Ala Lys Ile<br>               405              410             415 | 1248 |
| ctt tct aaa ttg cat aat cat gcc ccc tta tct tca cac aaa aaa atc<br>Leu Ser Lys Leu His Asn His Ala Pro Leu Ser Ser His Lys Lys Ile<br>           420                425             430 | 1296 |
| tat aat ctt aga gga gag tta gat tta aca tct cat aaa gat tta tta<br>Tyr Asn Leu Arg Gly Glu Leu Asp Leu Thr Ser His Lys Asp Leu Leu<br>             435                440             445 | 1344 |
| agt gat aat ccg aat cat tgg aga ctt att agg gga gac cat gtt gaa<br>Ser Asp Asn Pro Asn His Trp Arg Leu Ile Arg Gly Asp His Val Glu<br>450                   455              460 | 1392 |
| aaa ttt aat tta aag aat cca gag gaa tca gaa aag cta gga ttt gtt<br>Lys Phe Asn Leu Lys Asn Pro Glu Glu Ser Glu Lys Leu Gly Phe Val<br>465                   470              475             480 | 1440 |
| gac cat caa tta ttt att aaa aga atg gga aaa agt aat aag tta aga<br>Asp His Gln Leu Phe Ile Lys Arg Met Gly Lys Ser Asn Lys Leu Arg<br>             485                490             495 | 1488 |
| cac att aaa aac tgg aga ata aca ctt cca caa tgt tct tat atg aat<br>His Ile Lys Asn Trp Arg Ile Thr Leu Pro Gln Cys Ser Tyr Met Asn | 1536 |

|  |  |  |  |  |  |  |  |  |  |  |  |  |  |  |  |
|---|---|---|---|---|---|---|---|---|---|---|---|---|---|---|---|
|  |  |  |  |  | 500 |  |  |  |  | 505 |  |  |  |  | 510 |
| aaa | aag | aag | cgg | ata | gag | gca | tgc | ata | gta | gaa | cca | aat | aat | ata | att | 1584 |
| Lys | Lys | Lys | Arg | Ile | Glu | Ala | Cys | Ile | Val | Glu | Pro | Asn | Asn | Ile | Ile |
|  |  | 515 |  |  |  | 520 |  |  |  | 525 |  |  |  |  |  |
| gca | aat | tca | tgt | aat | tat | atc | act | tta | gaa | gat | tgt | aac | gaa | ttg | gta | 1632 |
| Ala | Asn | Ser | Cys | Asn | Tyr | Ile | Thr | Leu | Glu | Asp | Cys | Asn | Glu | Leu | Val |
| 530 |  |  |  |  | 535 |  |  |  |  | 540 |  |  |  |  |  |
| gac | aac | tta | ctg | tta | ctc | tgt | gca | att | ata | aat | agt | gct | gta | ata | gag | 1680 |
| Asp | Asn | Leu | Leu | Leu | Leu | Cys | Ala | Ile | Ile | Asn | Ser | Ala | Val | Ile | Glu |
| 545 |  |  |  |  | 550 |  |  |  |  | 555 |  |  |  |  | 560 |
| tgg | aga | ttt | aga | ttg | ttc | aat | agt | aat | aat | cat | gtg | tca | aat | tat | gag | 1728 |
| Trp | Arg | Phe | Arg | Leu | Phe | Asn | Ser | Asn | Asn | His | Val | Ser | Asn | Tyr | Glu |
|  |  |  |  | 565 |  |  |  |  | 570 |  |  |  |  | 575 |  |
| att | gat | gaa | ttt | cca | ata | ttt | aaa | ttt | gat | act | gaa | act | gaa | atg | ttg | 1776 |
| Ile | Asp | Glu | Phe | Pro | Ile | Phe | Lys | Phe | Asp | Thr | Glu | Thr | Glu | Met | Leu |
|  |  |  | 580 |  |  |  |  | 585 |  |  |  |  | 590 |  |  |
| act | atg | tta | aaa | ggt | ttt | ttg | cat | aag | ccc | ata | gaa | aat | tgg | tct | aaa | 1824 |
| Thr | Met | Leu | Lys | Gly | Phe | Leu | His | Lys | Pro | Ile | Glu | Asn | Trp | Ser | Lys |
|  |  | 595 |  |  |  |  | 600 |  |  |  |  | 605 |  |  |  |
| ata | gaa | gct | ctt | ata | gct | tta | atg | tat | gga | ttg | aat | ata | gaa | gat | atg | 1872 |
| Ile | Glu | Ala | Leu | Ile | Ala | Leu | Met | Tyr | Gly | Leu | Asn | Ile | Glu | Asp | Met |
| 610 |  |  |  |  | 615 |  |  |  |  | 620 |  |  |  |  |  |
| aaa | gta | ata | ctg | aat | gat | tta | gaa | tat | gaa | gat | aaa | gat | aaa | ata | tta | 1920 |
| Lys | Val | Ile | Leu | Asn | Asp | Leu | Glu | Tyr | Glu | Asp | Lys | Asp | Lys | Ile | Leu |
| 625 |  |  |  |  | 630 |  |  |  |  | 635 |  |  |  |  | 640 |
| aaa | tat | atg | gat | att | tat | caa | gag | aaa | ttt | agt | aat | aaa | gac | ttt | ata | 1968 |
| Lys | Tyr | Met | Asp | Ile | Tyr | Gln | Glu | Lys | Phe | Ser | Asn | Lys | Asp | Phe | Ile |
|  |  |  |  | 645 |  |  |  |  | 650 |  |  |  |  | 655 |  |
| gtt | tat | aac | cat | act | tta | cca | aca | ctt | tca | gaa | tta | gat | aaa | gag | atg | 2016 |
| Val | Tyr | Asn | His | Thr | Leu | Pro | Thr | Leu | Ser | Glu | Leu | Asp | Lys | Glu | Met |
|  |  |  | 660 |  |  |  |  | 665 |  |  |  |  | 670 |  |  |
| att | tca | tat | gtt | aaa | caa | ggg | ggg | aac | tgg | gag | gac | att | cct | gaa | act | 2064 |
| Ile | Ser | Tyr | Val | Lys | Gln | Gly | Gly | Asn | Trp | Glu | Asp | Ile | Pro | Glu | Thr |
|  |  | 675 |  |  |  |  | 680 |  |  |  |  | 685 |  |  |  |
| gtt | cct | tca | aag | aga | tta | gaa | cag | ata | aga | gaa | atg | agt | aag | aga | aga | 2112 |
| Val | Pro | Ser | Lys | Arg | Leu | Glu | Gln | Ile | Arg | Glu | Met | Ser | Lys | Arg | Arg |
|  | 690 |  |  |  |  | 695 |  |  |  |  | 700 |  |  |  |  |
| gga | aaa | gtt | agg | act | acc | tat | tat | ggt | aga | tta | aac | cct | aat | caa | cct | 2160 |
| Gly | Lys | Val | Arg | Thr | Thr | Tyr | Tyr | Gly | Arg | Leu | Asn | Pro | Asn | Gln | Pro |
| 705 |  |  |  |  | 710 |  |  |  |  | 715 |  |  |  |  | 720 |
| gct | tat | aca | ata | tcc | act | tat | ttt | aat | agg | ccg | gga | aat | gga | acg | aat | 2208 |
| Ala | Tyr | Thr | Ile | Ser | Thr | Tyr | Phe | Asn | Arg | Pro | Gly | Asn | Gly | Thr | Asn |
|  |  |  |  | 725 |  |  |  |  | 730 |  |  |  |  | 735 |  |
| att | cat | cct | tgg | gaa | aat | agg | acc | ata | agt | tgc | aga | gaa | gct | gcg | aga | 2256 |
| Ile | His | Pro | Trp | Glu | Asn | Arg | Thr | Ile | Ser | Cys | Arg | Glu | Ala | Ala | Arg |
|  |  |  | 740 |  |  |  |  | 745 |  |  |  |  | 750 |  |  |
| tta | caa | tca | ttt | cct | gat | agt | ttt | atc | ttc | tat | ggg | aag | gag | gga | gca | 2304 |
| Leu | Gln | Ser | Phe | Pro | Asp | Ser | Phe | Ile | Phe | Tyr | Gly | Lys | Glu | Gly | Ala |
|  |  | 755 |  |  |  |  | 760 |  |  |  |  | 765 |  |  |  |
| gtt | aga | aaa | cag | ata | ggt | aat | gcc | gtt | cct | cca | tta | tta | agt | tat | gct | 2352 |
| Val | Arg | Lys | Gln | Ile | Gly | Asn | Ala | Val | Pro | Pro | Leu | Leu | Ser | Tyr | Ala |
| 770 |  |  |  |  | 775 |  |  |  |  | 780 |  |  |  |  |  |
| tta | ggt | aag | aca | ata | aaa | gct | aaa | aca | ttt | gta | gat | tta | ttt | gct | gga | 2400 |
| Leu | Gly | Lys | Thr | Ile | Lys | Ala | Lys | Thr | Phe | Val | Asp | Leu | Phe | Ala | Gly |
| 785 |  |  |  |  | 790 |  |  |  |  | 795 |  |  |  |  | 800 |
| gca | ggc | gga | ctt | agc | tat | ggt | ttt | gaa | ctt | gct | gga | tta | gaa | ggg | atg | 2448 |
| Ala | Gly | Gly | Leu | Ser | Tyr | Gly | Phe | Glu | Leu | Ala | Gly | Leu | Glu | Gly | Met |
|  |  |  |  | 805 |  |  |  |  | 810 |  |  |  |  | 815 |  |
| gca | gcc | tta | gag | att | gat | aaa | gat | gcc | gct | gaa | act | tat | gca | aaa | aat | 2496 |

```
                Ala Ala Leu Glu Ile Asp Lys Asp Ala Ala Glu Thr Tyr Ala Lys Asn
                                820                 825                 830 cat tca tct aat ata gac gta ata gtc ggt gat atc aga agc cca gaa        2544
His Ser Ser Asn Ile Asp Val Ile Val Gly Asp Ile Arg Ser Pro Glu
            835                 840                 845 ata caa aat caa tta att gag tca gtg aaa aac aag tta aag ggt cga        2592
Ile Gln Asn Gln Leu Ile Glu Ser Val Lys Asn Lys Leu Lys Gly Arg
        850                 855                 860 act tta gat tta att gct ggt ggt ctt cct tgt caa ggc ttt tca aca        2640
Thr Leu Asp Leu Ile Ala Gly Gly Leu Pro Cys Gln Gly Phe Ser Thr
865                 870                 875                 880 gca gga tgg aga aag cca gat gat gag agg aat gct tta gtc act tat        2688
Ala Gly Trp Arg Lys Pro Asp Asp Glu Arg Asn Ala Leu Val Thr Tyr
                885                 890                 895 ttt ttg cag gtt gtt cag aag tta atg cca aat tac gtt tta ata gaa        2736
Phe Leu Gln Val Val Gln Lys Leu Met Pro Asn Tyr Val Leu Ile Glu
            900                 905                 910 aac gta gaa ggg ctt att aat atg aat aaa gga tta gta ctt aaa agt        2784
Asn Val Glu Gly Leu Ile Asn Met Asn Lys Gly Leu Val Leu Lys Ser
        915                 920                 925 att cat gaa gta tta gat gag ttg ggc tat att tac tat aag aat cct        2832
Ile His Glu Val Leu Asp Glu Leu Gly Tyr Ile Tyr Tyr Lys Asn Pro
930                 935                 940 tgg gta tta agt gcg gaa caa tat ggg gta cct caa atg aga aaa agg        2880
Trp Val Leu Ser Ala Glu Gln Tyr Gly Val Pro Gln Met Arg Lys Arg
945                 950                 955                 960 gtt ttt att gta gcc gca aaa aaa gga tta gaa tta cca aaa cca cca        2928
Val Phe Ile Val Ala Ala Lys Lys Gly Leu Glu Leu Pro Lys Pro Pro
                965                 970                 975 gtt caa tac ttt gac aag tgt ctc ggt aga cgt gaa aaa gaa tcg gat        2976
Val Gln Tyr Phe Asp Lys Cys Leu Gly Arg Arg Glu Lys Glu Ser Asp
            980                 985                 990 agg aaa act gat aga tat cca gta aca gtt gcg gaa gcc ttc ttt gga        3024
Arg Lys Thr Asp Arg Tyr Pro Val Thr Val Ala Glu Ala Phe Phe Gly
        995                 1000                1005 cta cct tgc tta tta agt ccg gta ttt act cct ccg tta gag att aac        3072
Leu Pro Cys Leu Leu Ser Pro Val Phe Thr Pro Pro Leu Glu Ile Asn
    1010                1015                1020 cct ttg tac agt caa tgg tgt aat aat att atc act act gaa gag ttt        3120
Pro Leu Tyr Ser Gln Trp Cys Asn Asn Ile Ile Thr Thr Glu Glu Phe
1025                1030                1035                1040 ctt aat aag aga ggt aaa att aaa att gag caa gaa gaa cta gat gct        3168
Leu Asn Lys Arg Gly Lys Ile Lys Ile Glu Gln Glu Glu Leu Asp Ala
                1045                1050                1055 cca caa cta aaa gta gaa caa cta gaa ttt acc ttt taa                    3207
Pro Gln Leu Lys Val Glu Gln Leu Glu Phe Thr Phe
            1060                1065

<210> SEQ ID NO 11
<211> LENGTH: 1068
<212> TYPE: PRT
<213> ORGANISM: Bacillus stearothermophilus B61

<400> SEQUENCE: 11

Met Asn Ser Leu Ser Leu Lys Asp Glu Met Glu Ile Trp Lys Gln Ala
1               5                   10                  15

Ser Asn Ile Arg Lys Lys Ile Ala Met Glu Thr Ala Ala Glu Phe Leu
            20                  25                  30

Asn Glu Phe Asn Ala Glu Lys Ala Leu Lys Gln Ile Lys Asn Ser Ile
        35                  40                  45
```

-continued

```
Leu Asn Pro Leu Tyr Glu Arg Asn Pro Phe Gln Asn Thr Leu Glu Lys
     50                  55                  60

Leu Ser Phe Ser Leu Tyr Leu Thr Glu Lys Ser Ile Asp Tyr Val Leu
 65                  70                  75                  80

Gln Met Glu Val Glu Pro Ile Lys Lys Leu Ser Tyr Ala Asn Phe Phe
                 85                  90                  95

Val Glu Ile Gly Ala Arg Glu Phe Ile Ser Pro Phe His Pro Asp Lys
                100                 105                 110

Ile Glu Lys Asn Leu Thr Ala Ser Lys Ala Tyr Gly Tyr Phe Phe Thr
            115                 120                 125

Pro Ile Ser Leu Gly Thr Arg Met Val Lys Leu Ala Leu Lys Asp Lys
    130                 135                 140

Pro Lys Asn Leu Lys Ser Ile Val Asp Pro Ala Cys Gly Ile Gly Ser
145                 150                 155                 160

Leu Leu Ala Leu Ala Leu Ile Tyr Asn Pro Glu Ile Glu Asn Val Val
                165                 170                 175

Gly Ile Glu Leu Asp Ser Phe Thr Ala Asn Ile Ser His Lys Leu Leu
                180                 185                 190

Val Arg Ile Ser Lys Asp Leu Gly Ile Thr Pro Lys Ile Lys Ile Ile
            195                 200                 205

Asn Gln Asn Phe Leu Asp Tyr Val Leu Asn Tyr Glu Glu His Lys
    210                 215                 220

Glu Lys Phe Asp Leu Leu Ile Met Asn Pro Pro Tyr Gly Arg Val Arg
225                 230                 235                 240

Phe Leu Lys Asn Ser Leu Thr Asn Lys Glu Thr Lys Ser Gly Leu Thr
                245                 250                 255

Glu Gly Ile Ser Glu Leu Glu Lys Lys Leu Arg Glu Glu Thr Ile Leu
                260                 265                 270

Asn Ala Ala Asp Leu Arg Lys Lys Phe Ala Ser Val Gly Leu Gly Lys
            275                 280                 285

Gly Thr Pro Glu Tyr Ser Lys Val Phe Leu Ala Ile Ser Thr Lys Ile
    290                 295                 300

Val Lys Gln Asn Gly Tyr Val Ile Ala Ile Thr Pro Ser Ser Trp Leu
305                 310                 315                 320

Gly Asp Glu Ser Gly Arg Glu Leu Arg Lys Tyr Leu Val Glu Asn His
                325                 330                 335

Gly Ile Ser Cys Ile Trp Asn Phe Lys Glu Ser Ala Lys Leu Phe Ser
                340                 345                 350

Gly Val Asn Gln Pro Thr Thr Val Val Lys Ile Lys Val Asn Ser Asn
            355                 360                 365

Glu Ser Lys Ile Glu Ile Gln Gly Pro Leu Ser Ser Leu Glu Glu Leu
    370                 375                 380

Gly Arg Asp Ile Gln Tyr Leu Asp Thr Cys Asn Ile Lys Lys Tyr Ser
385                 390                 395                 400

Pro Glu Trp Tyr Arg Ile Pro Gln Cys Gly Asn Glu Arg Ala Lys Ile
                405                 410                 415

Leu Ser Lys Leu His Asn His Ala Pro Leu Ser Ser His Lys Lys Ile
                420                 425                 430

Tyr Asn Leu Arg Gly Glu Leu Asp Leu Thr Ser His Lys Asp Leu Leu
            435                 440                 445

Ser Asp Asn Pro Asn His Trp Arg Leu Ile Arg Gly Asp His Val Glu
    450                 455                 460
```

-continued

```
Lys Phe Asn Leu Lys Asn Pro Glu Glu Ser Glu Lys Leu Gly Phe Val
465                 470                 475                 480

Asp His Gln Leu Phe Ile Lys Arg Met Gly Lys Ser Asn Lys Leu Arg
                485                 490                 495

His Ile Lys Asn Trp Arg Ile Thr Leu Pro Gln Cys Ser Tyr Met Asn
            500                 505                 510

Lys Lys Lys Arg Ile Glu Ala Cys Ile Val Glu Pro Asn Asn Ile Ile
        515                 520                 525

Ala Asn Ser Cys Asn Tyr Ile Thr Leu Glu Asp Cys Asn Glu Leu Val
    530                 535                 540

Asp Asn Leu Leu Leu Cys Ala Ile Ile Asn Ser Ala Val Ile Glu
545                 550                 555                 560

Trp Arg Phe Arg Leu Phe Asn Ser Asn Asn His Val Ser Asn Tyr Glu
                565                 570                 575

Ile Asp Glu Phe Pro Ile Phe Lys Phe Asp Thr Glu Thr Glu Met Leu
            580                 585                 590

Thr Met Leu Lys Gly Phe Leu His Lys Pro Ile Glu Asn Trp Ser Lys
        595                 600                 605

Ile Glu Ala Leu Ile Ala Leu Met Tyr Gly Leu Asn Ile Glu Asp Met
    610                 615                 620

Lys Val Ile Leu Asn Asp Leu Glu Tyr Glu Asp Lys Asp Lys Ile Leu
625                 630                 635                 640

Lys Tyr Met Asp Ile Tyr Gln Glu Lys Phe Ser Asn Lys Asp Phe Ile
                645                 650                 655

Val Tyr Asn His Thr Leu Pro Thr Leu Ser Glu Leu Asp Lys Glu Met
            660                 665                 670

Ile Ser Tyr Val Lys Gln Gly Gly Asn Trp Glu Asp Ile Pro Glu Thr
        675                 680                 685

Val Pro Ser Lys Arg Leu Glu Gln Ile Arg Glu Met Ser Lys Arg Arg
    690                 695                 700

Gly Lys Val Arg Thr Thr Tyr Tyr Gly Arg Leu Asn Pro Asn Gln Pro
705                 710                 715                 720

Ala Tyr Thr Ile Ser Thr Tyr Phe Asn Arg Pro Gly Asn Gly Thr Asn
                725                 730                 735

Ile His Pro Trp Glu Asn Arg Thr Ile Ser Cys Arg Glu Ala Ala Arg
            740                 745                 750

Leu Gln Ser Phe Pro Asp Ser Phe Ile Phe Tyr Gly Lys Glu Gly Ala
        755                 760                 765

Val Arg Lys Gln Ile Gly Asn Ala Val Pro Pro Leu Leu Ser Tyr Ala
    770                 775                 780

Leu Gly Lys Thr Ile Lys Ala Lys Thr Phe Val Asp Leu Phe Ala Gly
785                 790                 795                 800

Ala Gly Gly Leu Ser Tyr Gly Phe Glu Leu Ala Gly Leu Glu Gly Met
                805                 810                 815

Ala Ala Leu Glu Ile Asp Lys Asp Ala Ala Glu Thr Tyr Ala Lys Asn
            820                 825                 830

His Ser Ser Asn Ile Asp Val Ile Val Gly Asp Ile Arg Ser Pro Glu
        835                 840                 845

Ile Gln Asn Gln Leu Ile Glu Ser Val Lys Asn Leu Lys Gly Arg
    850                 855                 860

Thr Leu Asp Leu Ile Ala Gly Gly Leu Pro Cys Gln Gly Phe Ser Thr
865                 870                 875                 880

Ala Gly Trp Arg Lys Pro Asp Asp Glu Arg Asn Ala Leu Val Thr Tyr
```

-continued

```
                    885                 890                 895
Phe Leu Gln Val Val Gln Lys Leu Met Pro Asn Tyr Val Leu Ile Glu
        900                 905                 910
Asn Val Glu Gly Leu Ile Asn Met Asn Lys Gly Leu Val Leu Lys Ser
            915                 920                 925
Ile His Glu Val Leu Asp Glu Leu Gly Tyr Ile Tyr Tyr Lys Asn Pro
        930                 935                 940
Trp Val Leu Ser Ala Glu Gln Tyr Gly Val Pro Gln Met Arg Lys Arg
945                 950                 955                 960
Val Phe Ile Val Ala Ala Lys Lys Gly Leu Glu Leu Pro Lys Pro Pro
            965                 970                 975
Val Gln Tyr Phe Asp Lys Cys Leu Gly Arg Arg Glu Lys Glu Ser Asp
        980                 985                 990
Arg Lys Thr Asp Arg Tyr Pro Val Thr Val Ala Glu Ala Phe Phe Gly
        995                 1000                1005
Leu Pro Cys Leu Leu Ser Pro Val Phe Thr Pro Pro Leu Glu Ile Asn
    1010                1015                1020
Pro Leu Tyr Ser Gln Trp Cys Asn Asn Ile Ile Thr Thr Glu Glu Phe
1025                1030                1035                1040
Leu Asn Lys Arg Gly Lys Ile Lys Ile Glu Gln Glu Leu Asp Ala
            1045                1050                1055
Pro Gln Leu Lys Val Glu Gln Leu Glu Phe Thr Phe
            1060                1065

<210> SEQ ID NO 12
<211> LENGTH: 1593
<212> TYPE: DNA
<213> ORGANISM: Bacillus stearothermophilus B61
<220> FEATURE:
<221> NAME/KEY: CDS
<222> LOCATION: (1)..(1593)

<400> SEQUENCE: 12 ttg gct aaa tac gga cgt gga aag ttt tta cct cat caa aac tat atc     48
Met Ala Lys Tyr Gly Arg Gly Lys Phe Leu Pro His Gln Asn Tyr Ile
1               5                   10                  15 gat tat atg cat ttt ata gtg aac cat aag aat tat tct ggt atg cca     96
Asp Tyr Met His Phe Ile Val Asn His Lys Asn Tyr Ser Gly Met Pro
                20                  25                  30 aac gct att gga gag gat gga aga ata aat tgg cag gta agc tct gga    144
Asn Ala Ile Gly Glu Asp Gly Arg Ile Asn Trp Gln Val Ser Ser Gly
            35                  40                  45 aaa aca acg tct ttt tat gaa tat tat caa gca aga ttt gaa tgg tgg    192
Lys Thr Thr Ser Phe Tyr Glu Tyr Tyr Gln Ala Arg Phe Glu Trp Trp
        50                  55                  60 gag aag aaa gct gat gaa ctt aat tta cct gga acg ggt aat tca aac    240
Glu Lys Lys Ala Asp Glu Leu Asn Leu Pro Gly Thr Gly Asn Ser Asn
65                  70                  75                  80 aaa agg ttt tct tta gca gca agg tta att cat cct aca gga caa agg    288
Lys Arg Phe Ser Leu Ala Ala Arg Leu Ile His Pro Thr Gly Gln Arg
                85                  90                  95 ccg tgt aga tta tgt ggt aag tac caa tat gtt ggt tac atg tat gtt    336
Pro Cys Arg Leu Cys Gly Lys Tyr Gln Tyr Val Gly Tyr Met Tyr Val
            100                 105                 110 tca cac aac ctt tac aaa cga tgg agt aag ata aca ggt aga gaa gac    384
Ser His Asn Leu Tyr Lys Arg Trp Ser Lys Ile Thr Gly Arg Glu Asp
        115                 120                 125 ctt ttt ttt aaa aaa cag aat atc att gag gca gct aac att ttt aaa    432
```

```
                                      -continued

Leu Phe Phe Lys Lys Gln Asn Ile Ile Glu Ala Ala Asn Ile Phe Lys
    130                 135                 140 tct att atg gga gaa caa gca ctt att aat gaa tta aca acc att ttt     480
Ser Ile Met Gly Glu Gln Ala Leu Ile Asn Glu Leu Thr Thr Ile Phe
145                 150                 155                 160 cca gaa aga aaa gat tat ttc aac aga tta cca aac att gaa gat ttc     528
Pro Glu Arg Lys Asp Tyr Phe Asn Arg Leu Pro Asn Ile Glu Asp Phe
                165                 170                 175 ttt gta agt tct agt cac ata aaa aat aat gga aat tat att agt cca     576
Phe Val Ser Ser Ser His Ile Lys Asn Asn Gly Asn Tyr Ile Ser Pro
            180                 185                 190 gga ttt atg gct aat ccg cct gac cga cta gac gga ttt cac gat tat     624
Gly Phe Met Ala Asn Pro Pro Asp Arg Leu Asp Gly Phe His Asp Tyr
        195                 200                 205 gga atc tgt tgt agg aaa gaa aaa gac cca ggg cga cat gac gat aac     672
Gly Ile Cys Cys Arg Lys Glu Lys Asp Pro Gly Arg His Asp Asp Asn
    210                 215                 220 atg aga cta tat aat cat gat aga cgt gct ttt atg tgg tgg tca gaa     720
Met Arg Leu Tyr Asn His Asp Arg Arg Ala Phe Met Trp Trp Ser Glu
225                 230                 235                 240 ggt gat tgg gca ctt gca gac gca cta tat aat aaa gct ggg gct gga     768
Gly Asp Trp Ala Leu Ala Asp Ala Leu Tyr Asn Lys Ala Gly Ala Gly
                245                 250                 255 aaa tgt gct gac cca gat tgt caa aaa gaa gtt gaa aaa ata agc cct     816
Lys Cys Ala Asp Pro Asp Cys Gln Lys Glu Val Glu Lys Ile Ser Pro
            260                 265                 270 gac cat gtt ggc cct atc tct tgt ggt ttt aaa cag att cct ttt ttt     864
Asp His Val Gly Pro Ile Ser Cys Gly Phe Lys Gln Ile Pro Phe Phe
        275                 280                 285 aaa cca ctc tgt gca tca tgt aac tca gca aaa aat cgt agg ttt tca     912
Lys Pro Leu Cys Ala Ser Cys Asn Ser Ala Lys Asn Arg Arg Phe Ser
    290                 295                 300 tat caa gat gta aag gaa tta tta aaa tat gaa aac tac aca gga gat     960
Tyr Gln Asp Val Lys Glu Leu Leu Lys Tyr Glu Asn Tyr Thr Gly Asp
305                 310                 315                 320 tcg gtt gct tca tgg caa gtg cgg gct tta tgg gat aac tgt aaa cat    1008
Ser Val Ala Ser Trp Gln Val Arg Ala Leu Trp Asp Asn Cys Lys His
                325                 330                 335 tta gta aaa aat gac gat gat tcc aaa tta ctt agc aat tta atg aga    1056
Leu Val Lys Asn Asp Asp Asp Ser Lys Leu Leu Ser Asn Leu Met Arg
            340                 345                 350 agc ttg caa gac tac tat tta cgg tct cta tat aaa ttg ttt tcg aat    1104
Ser Leu Gln Asp Tyr Tyr Leu Arg Ser Leu Tyr Lys Leu Phe Ser Asn
        355                 360                 365 ggc ttt gca cat ctt cta tct tac ttc ctc aca ccc gaa tat gca cat    1152
Gly Phe Ala His Leu Leu Ser Tyr Phe Leu Thr Pro Glu Tyr Ala His
    370                 375                 380 tat aaa att act ttt gag gga tta aat aca agc act cta gaa tat gaa    1200
Tyr Lys Ile Thr Phe Glu Gly Leu Asn Thr Ser Thr Leu Glu Tyr Glu
385                 390                 395                 400 cga tac tac aaa act ttt aaa aag act aaa tcg acg tct agt ttg gct    1248
Arg Tyr Tyr Lys Thr Phe Lys Lys Thr Lys Ser Thr Ser Ser Leu Ala
                405                 410                 415 gca cga att gtt aga att gca ttt gag gaa cta gaa ata tat aat tct    1296
Ala Arg Ile Val Arg Ile Ala Phe Glu Glu Leu Glu Ile Tyr Asn Ser
            420                 425                 430 aag gat ata aat gag aga aag tta att aaa ttt gac act tca agt tgg    1344
Lys Asp Ile Asn Glu Arg Lys Leu Ile Lys Phe Asp Thr Ser Ser Trp
        435                 440                 445
```

```
gaa aag gac ttt gag aat ata ata tcc tat gct acc aaa aac tta tct    1392
Glu Lys Asp Phe Glu Asn Ile Ile Ser Tyr Ala Thr Lys Asn Leu Ser
    450                 455                 460 ttg gat gaa gaa gca tca aaa tgg aat aag gtt tta act gat aag aat    1440
Leu Asp Glu Glu Ala Ser Lys Trp Asn Lys Val Leu Thr Asp Lys Asn
465                 470                 475                 480 tta agc tca acc gag aaa gac aag aaa att tcc tcc tta ctt gaa gat    1488
Leu Ser Ser Thr Glu Lys Asp Lys Lys Ile Ser Ser Leu Leu Glu Asp
                485                 490                 495 aag aac tat gaa gtt tat aag aaa caa ttt tat atc ctc aaa gat ttg    1536
Lys Asn Tyr Glu Val Tyr Lys Lys Gln Phe Tyr Ile Leu Lys Asp Leu
            500                 505                 510 ctt gta gaa cac ttt aac aaa att ggg gag cag att gct aaa gat tat    1584
Leu Val Glu His Phe Asn Lys Ile Gly Glu Gln Ile Ala Lys Asp Tyr
        515                 520                 525 atg aaa taa                                                        1593
Met Lys
    530
```

<210> SEQ ID NO 13
<211> LENGTH: 530
<212> TYPE: PRT
<213> ORGANISM: Bacillus stearothermophilus B61

<400> SEQUENCE: 13

```
Met Ala Lys Tyr Gly Arg Gly Lys Phe Leu Pro His Gln Asn Tyr Ile
 1               5                  10                  15

Asp Tyr Met His Phe Ile Val Asn His Lys Asn Tyr Ser Gly Met Pro
            20                  25                  30

Asn Ala Ile Gly Glu Asp Gly Arg Ile Asn Trp Gln Val Ser Ser Gly
        35                  40                  45

Lys Thr Thr Ser Phe Tyr Glu Tyr Tyr Gln Ala Arg Phe Glu Trp Trp
    50                  55                  60

Glu Lys Lys Ala Asp Glu Leu Asn Leu Pro Gly Thr Gly Asn Ser Asn
65                  70                  75                  80

Lys Arg Phe Ser Leu Ala Ala Arg Leu Ile His Pro Thr Gly Gln Arg
                85                  90                  95

Pro Cys Arg Leu Cys Gly Lys Tyr Gln Tyr Val Gly Tyr Met Tyr Val
            100                 105                 110

Ser His Asn Leu Tyr Lys Arg Trp Ser Lys Ile Thr Gly Arg Glu Asp
        115                 120                 125

Leu Phe Phe Lys Lys Gln Asn Ile Ile Glu Ala Asn Ile Phe Lys
    130                 135                 140

Ser Ile Met Gly Glu Gln Ala Leu Ile Asn Glu Leu Thr Thr Ile Phe
145                 150                 155                 160

Pro Glu Arg Lys Asp Tyr Phe Asn Arg Leu Pro Asn Ile Glu Asp Phe
                165                 170                 175

Phe Val Ser Ser Ser His Ile Lys Asn Asn Gly Asn Tyr Ile Ser Pro
            180                 185                 190

Gly Phe Met Ala Asn Pro Pro Asp Arg Leu Asp Gly Phe His Asp Tyr
        195                 200                 205

Gly Ile Cys Cys Arg Lys Glu Lys Asp Pro Gly Arg His Asp Asp Asn
    210                 215                 220

Met Arg Leu Tyr Asn His Asp Arg Arg Ala Phe Met Trp Trp Ser Glu
225                 230                 235                 240

Gly Asp Trp Ala Leu Ala Asp Ala Leu Tyr Asn Lys Ala Gly Ala Gly
                245                 250                 255
```

-continued

```
Lys Cys Ala Asp Pro Asp Cys Gln Lys Glu Val Glu Lys Ile Ser Pro
            260                 265                 270

Asp His Val Gly Pro Ile Ser Cys Gly Phe Lys Gln Ile Pro Phe Phe
            275                 280                 285

Lys Pro Leu Cys Ala Ser Cys Asn Ser Ala Lys Asn Arg Arg Phe Ser
            290                 295                 300

Tyr Gln Asp Val Lys Glu Leu Lys Tyr Glu Asn Tyr Thr Gly Asp
305                 310                 315                 320

Ser Val Ala Ser Trp Gln Val Arg Ala Leu Trp Asp Asn Cys Lys His
                325                 330                 335

Leu Val Lys Asn Asp Asp Ser Lys Leu Leu Ser Asn Leu Met Arg
            340                 345                 350

Ser Leu Gln Asp Tyr Tyr Leu Arg Ser Leu Tyr Lys Leu Phe Ser Asn
            355                 360                 365

Gly Phe Ala His Leu Leu Ser Tyr Phe Leu Thr Pro Glu Tyr Ala His
            370                 375                 380

Tyr Lys Ile Thr Phe Glu Gly Leu Asn Thr Ser Thr Leu Glu Tyr Glu
385                 390                 395                 400

Arg Tyr Tyr Lys Thr Phe Lys Lys Thr Lys Ser Thr Ser Ser Leu Ala
                405                 410                 415

Ala Arg Ile Val Arg Ile Ala Phe Glu Glu Leu Glu Ile Tyr Asn Ser
            420                 425                 430

Lys Asp Ile Asn Glu Arg Lys Leu Ile Lys Phe Asp Thr Ser Ser Trp
            435                 440                 445

Glu Lys Asp Phe Glu Asn Ile Ile Ser Tyr Ala Thr Lys Asn Leu Ser
450                 455                 460

Leu Asp Glu Glu Ala Ser Lys Trp Asn Lys Val Leu Thr Asp Lys Asn
465                 470                 475                 480

Leu Ser Ser Thr Glu Lys Asp Lys Lys Ile Ser Ser Leu Leu Glu Asp
                485                 490                 495

Lys Asn Tyr Glu Val Tyr Lys Lys Gln Phe Tyr Ile Leu Lys Asp Leu
            500                 505                 510

Leu Val Glu His Phe Asn Lys Ile Gly Glu Gln Ile Ala Lys Asp Tyr
            515                 520                 525

Met Lys
    530

<210> SEQ ID NO 14
<211> LENGTH: 48
<212> TYPE: DNA
<213> ORGANISM: Bacillus stearothermophilus B61

<400> SEQUENCE: 14
taaggatccg gaggtaaata aatgaactcc ttatcactaa aagatgaa            48

<210> SEQ ID NO 15
<211> LENGTH: 39
<212> TYPE: DNA
<213> ORGANISM: Bacillus stearothermophilus B61

<400> SEQUENCE: 15
atgaaagtcg accccgtaat tttacgggct ttttaaaa                       39

<210> SEQ ID NO 16
<211> LENGTH: 48
<212> TYPE: DNA
```

```
<213> ORGANISM: Bacillus stearothermophilus B61

<400> SEQUENCE: 16
tatggatccg gaggtaaata aatgaaagta atactgaatg atttagaa          48

<210> SEQ ID NO 17
<211> LENGTH: 24
<212> TYPE: DNA
<213> ORGANISM: Bacillus stearothermophilus B61

<400> SEQUENCE: 17
cccataaagc ccgcacttgc catg                                    24

<210> SEQ ID NO 18
<211> LENGTH: 24
<212> TYPE: DNA
<213> ORGANISM: Bacillus stearothermophilus B61

<400> SEQUENCE: 18
tgacgatgat tccaaattac ttag                                    24

<210> SEQ ID NO 19
<211> LENGTH: 27
<212> TYPE: DNA
<213> ORGANISM: Bacillus stearothermophilus B61

<400> SEQUENCE: 19
ctttccctaa agctacttaa ttgaact                                 27

<210> SEQ ID NO 20
<211> LENGTH: 27
<212> TYPE: DNA
<213> ORGANISM: Bacillus stearothermophilus B61

<400> SEQUENCE: 20
ttataacaac aatacacaag ctttccc                                 27

<210> SEQ ID NO 21
<211> LENGTH: 24
<212> TYPE: DNA
<213> ORGANISM: Bacillus stearothermophilus B61

<400> SEQUENCE: 21
tcttacccca tccttcagac aaac                                    24

<210> SEQ ID NO 22
<211> LENGTH: 25
<212> TYPE: DNA
<213> ORGANISM: Bacillus stearothermophilus B61

<400> SEQUENCE: 22
aagacccagg gcgacatgac gataa                                   25

<210> SEQ ID NO 23
<211> LENGTH: 24
<212> TYPE: DNA
<213> ORGANISM: Bacillus stearothermophilus B61

<400> SEQUENCE: 23
tgtatatgga catattggaa agat                                    24

<210> SEQ ID NO 24
<211> LENGTH: 39
```

```
-continued

<212> TYPE: DNA
<213> ORGANISM: Bacillus stearothermophilus B61

<400> SEQUENCE: 24
gggtagattc atatggctaa atacggacgt ggaaagttt                                39

<210> SEQ ID NO 25
<211> LENGTH: 36
<212> TYPE: DNA
<213> ORGANISM: Bacillus stearothermophilus B61

<400> SEQUENCE: 25
gctggatcct catataatct ttagcaatct gctccc                                  36

<210> SEQ ID NO 26
<211> LENGTH: 42
<212> TYPE: DNA
<213> ORGANISM: Bacillus stearothermophilus B61

<400> SEQUENCE: 26
aagggatccg gaggtaaata aatggctaaa tacggaaagt tt                           42

<210> SEQ ID NO 27
<211> LENGTH: 5
<212> TYPE: DNA
<213> ORGANISM: Bacillus stearothermophilus B61

<400> SEQUENCE: 27 gtctc                                                                     5
```